(12) United States Patent
Park et al.

(10) Patent No.: US 8,194,968 B2
(45) Date of Patent: Jun. 5, 2012

(54) METHODS AND SYSTEMS FOR USING ELECTRICAL INFORMATION FOR A DEVICE BEING FABRICATED ON A WAFER TO PERFORM ONE OR MORE DEFECT-RELATED FUNCTIONS

(75) Inventors: Allen Park, San Jose, CA (US); Peter Rose, Boulder Creek, CA (US); Ellis Chang, Saratoga, CA (US); Brian Duffy, San Jose, CA (US); Mark McCord, Mountain View, CA (US); Gordon Abbott, Pleasanton, CA (US)

(73) Assignee: KLA-Tencor Corp., San Jose, CA (US)

( * ) Notice: Subject to any disclaimer, the term of this patent is extended or adjusted under 35 U.S.C. 154(b) by 1186 days.

(21) Appl. No.: 11/970,294

(22) Filed: Jan. 7, 2008

(65) Prior Publication Data

US 2008/0167829 A1    Jul. 10, 2008

Related U.S. Application Data

(60) Provisional application No. 60/883,617, filed on Jan. 5, 2007.

(51) Int. Cl.
*G06K 9/00* (2006.01)

(52) U.S. Cl. ...................................... 382/145
(58) Field of Classification Search ........................ None
See application file for complete search history.

(56) References Cited

U.S. PATENT DOCUMENTS

| | | | |
|---|---|---|---|
| 3,495,269 A | 2/1970 | Mutschler et al. |
| 3,496,352 A | 2/1970 | Jugle |
| 3,909,602 A | 9/1975 | Micka |
| 4,015,203 A | 3/1977 | Verkuil |
| 4,247,203 A | 1/1981 | Levy et al. |
| 4,347,001 A | 8/1982 | Levy et al. |
| 4,378,159 A | 3/1983 | Galbraith |
| 4,448,532 A | 5/1984 | Joseph et al. |
| 4,532,650 A | 7/1985 | Wihl et al. |
| 4,555,798 A | 11/1985 | Broadbent, Jr. et al. |
| 4,578,810 A | 3/1986 | MacFarlane et al. |
| 4,579,455 A | 4/1986 | Levy et al. |
| 4,595,289 A | 6/1986 | Feldman et al. |
| 4,599,558 A | 7/1986 | Castellano et al. |
| 4,633,504 A | 12/1986 | Wihl |

(Continued)

FOREIGN PATENT DOCUMENTS

EP        0032197        7/1981

(Continued)

OTHER PUBLICATIONS

International Search Report & Written Opinion, PCT/US2008/066328, mailed Oct. 1, 2009.

(Continued)

*Primary Examiner* — Tu Nguyen

(74) *Attorney, Agent, or Firm* — Ann Marie Mewherter

(57) ABSTRACT

Various methods and systems for using electrical information for a device being fabricated on a wafer to perform one or more defect-related functions are provided. One computer-implemented method includes using electrical information for a device being fabricated on a wafer to perform one or more defect-related functions. The one or more defect-related functions include one or more post-mask, defect-related functions.

85 Claims, 1 Drawing Sheet

U.S. PATENT DOCUMENTS

| | | | |
|---|---|---|---|
| 4,641,353 A | 2/1987 | Kobayashi | |
| 4,641,967 A | 2/1987 | Pecan | |
| 4,734,721 A | 3/1988 | Boyer et al. | |
| 4,748,327 A | 5/1988 | Shinozaki et al. | |
| 4,758,094 A | 7/1988 | Wihl | |
| 4,766,324 A | 8/1988 | Saadat et al. | |
| 4,799,175 A | 1/1989 | Sano et al. | |
| 4,805,123 A | 2/1989 | Specht et al. | |
| 4,812,756 A | 3/1989 | Curtis et al. | |
| 4,814,829 A | 3/1989 | Kosugi et al. | |
| 4,817,123 A | 3/1989 | Sones et al. | |
| 4,845,558 A | 7/1989 | Tsai et al. | |
| 4,877,326 A | 10/1989 | Chadwick et al. | |
| 4,926,489 A | 5/1990 | Danielson et al. | |
| 4,928,313 A | 5/1990 | Leonard et al. | |
| 5,046,109 A | 9/1991 | Fujimori et al. | |
| 5,124,927 A | 6/1992 | Hopewell et al. | |
| 5,189,481 A | 2/1993 | Jann et al. | |
| 5,355,212 A | 10/1994 | Wells et al. | |
| 5,444,480 A | 8/1995 | Sumita | |
| 5,453,844 A | 9/1995 | George et al. | |
| 5,459,520 A | 10/1995 | Sasaki | |
| 5,481,624 A | 1/1996 | Kamon | |
| 5,485,091 A | 1/1996 | Verkuil | |
| 5,497,381 A | 3/1996 | O'Donoghue et al. | |
| 5,528,153 A | 6/1996 | Taylor et al. | |
| 5,544,256 A | 8/1996 | Brecher et al. | |
| 5,563,702 A | 10/1996 | Emery et al. | |
| 5,572,598 A | 11/1996 | Wihl et al. | |
| 5,578,821 A | 11/1996 | Meisberger et al. | |
| 5,594,247 A | 1/1997 | Verkuil et al. | |
| 5,608,538 A | 3/1997 | Edger et al. | |
| 5,619,548 A | 4/1997 | Koppel | |
| 5,621,519 A | 4/1997 | Frost et al. | |
| 5,644,223 A | 7/1997 | Verkuil | |
| 5,650,731 A | 7/1997 | Fung | |
| 5,661,408 A | 8/1997 | Kamieniecki et al. | |
| 5,689,614 A | 11/1997 | Gronet et al. | |
| 5,694,478 A | 12/1997 | Braier et al. | |
| 5,696,835 A | 12/1997 | Hennessey et al. | |
| 5,703,969 A | 12/1997 | Hennessey et al. | |
| 5,737,072 A | 4/1998 | Emery et al. | |
| 5,742,658 A | 4/1998 | Tiffin et al. | |
| 5,754,678 A | 5/1998 | Hawthorne et al. | |
| 5,767,691 A | 6/1998 | Verkuil | |
| 5,767,693 A | 6/1998 | Verkuil | |
| 5,771,317 A | 6/1998 | Edgar | |
| 5,773,989 A | 6/1998 | Edelman et al. | |
| 5,774,179 A | 6/1998 | Chevrette et al. | |
| 5,795,685 A | 8/1998 | Liebmann et al. | |
| 5,822,218 A | 10/1998 | Moosa et al. | |
| 5,831,865 A | 11/1998 | Berezin et al. | |
| 5,834,941 A | 11/1998 | Verkuil | |
| 5,852,232 A | 12/1998 | Samsavar et al. | |
| 5,866,806 A | 2/1999 | Samsavar et al. | |
| 5,874,733 A | 2/1999 | Silver et al. | |
| 5,884,242 A | 3/1999 | Meier et al. | |
| 5,889,593 A | 3/1999 | Bareket | |
| 5,917,332 A | 6/1999 | Chen et al. | |
| 5,932,377 A | 8/1999 | Ferguson et al. | |
| 5,940,458 A | 8/1999 | Suk | |
| 5,948,972 A | 9/1999 | Samsavar et al. | |
| 5,955,661 A | 9/1999 | Samsavar et al. | |
| 5,965,306 A | 10/1999 | Mansfield et al. | |
| 5,978,501 A | 11/1999 | Badger et al. | |
| 5,980,187 A | 11/1999 | Verhovsky | |
| 5,986,263 A | 11/1999 | Hiroi et al. | |
| 5,991,699 A | 11/1999 | Kulkarni et al. | |
| 5,999,003 A | 12/1999 | Steffan et al. | |
| 6,011,404 A | 1/2000 | Ma et al. | |
| 6,014,461 A | 1/2000 | Hennessey et al. | |
| 6,040,912 A | 3/2000 | Zika et al. | |
| 6,052,478 A | 4/2000 | Wihl et al. | |
| 6,060,709 A | 5/2000 | Verkuil et al. | |
| 6,072,320 A | 6/2000 | Verkuil | |
| 6,076,465 A | 6/2000 | Vacca et al. | |
| 6,078,738 A | 6/2000 | Garza et al. | |
| 6,091,257 A | 7/2000 | Verkuil et al. | |
| 6,091,846 A | 7/2000 | Lin et al. | |
| 6,097,196 A | 8/2000 | Verkuil et al. | |
| 6,097,887 A | 8/2000 | Hardikar et al. | |
| 6,104,206 A | 8/2000 | Verkuil | |
| 6,104,835 A | 8/2000 | Han | |
| 6,117,598 A | 9/2000 | Imai | |
| 6,121,783 A | 9/2000 | Horner et al. | |
| 6,122,017 A | 9/2000 | Taubman | |
| 6,122,046 A | 9/2000 | Almogy | |
| 6,137,570 A | 10/2000 | Chuang et al. | |
| 6,141,038 A | 10/2000 | Young et al. | |
| 6,146,627 A | 11/2000 | Muller | |
| 6,171,737 B1 | 1/2001 | Phan et al. | |
| 6,175,645 B1 | 1/2001 | Elyasaf et al. | |
| 6,184,929 B1 | 2/2001 | Noda et al. | |
| 6,184,976 B1 | 2/2001 | Park et al. | |
| 6,191,605 B1 | 2/2001 | Miller et al. | |
| 6,201,999 B1 | 3/2001 | Jevtic | |
| 6,202,029 B1 | 3/2001 | Verkuil et al. | |
| 6,205,239 B1 | 3/2001 | Lin et al. | |
| 6,224,638 B1 | 5/2001 | Jevtic et al. | |
| 6,233,719 B1 | 5/2001 | Hardikar et al. | |
| 6,246,787 B1 | 6/2001 | Hennessey et al. | |
| 6,248,485 B1 | 6/2001 | Cuthbert | |
| 6,248,486 B1 | 6/2001 | Dirksen et al. | |
| 6,259,960 B1 | 7/2001 | Inokuchi | |
| 6,266,437 B1 | 7/2001 | Elchel et al. | |
| 6,267,005 B1 | 7/2001 | Samsavar et al. | |
| 6,268,093 B1 | 7/2001 | Kenan et al. | |
| 6,272,236 B1 | 8/2001 | Pierrat et al. | |
| 6,282,309 B1 | 8/2001 | Emery | |
| 6,292,582 B1 | 9/2001 | Lin et al. | |
| 6,324,298 B1 | 11/2001 | O'Dell et al. | |
| 6,344,640 B1 | 2/2002 | Rhoads | |
| 6,363,166 B1 | 3/2002 | Wihl et al. | |
| 6,373,975 B1 | 4/2002 | Bula et al. | |
| 6,388,747 B2 | 5/2002 | Nara et al. | |
| 6,393,602 B1 | 5/2002 | Atchison et al. | |
| 6,415,421 B2 | 7/2002 | Anderson et al. | |
| 6,445,199 B1 | 9/2002 | Satya et al. | |
| 6,451,690 B1 | 9/2002 | Matsumoto | |
| 6,466,314 B1 | 10/2002 | Lehman | |
| 6,466,315 B1 | 10/2002 | Karpol et al. | |
| 6,470,489 B1 | 10/2002 | Chang et al. | |
| 6,483,938 B1 | 11/2002 | Hennessey et al. | |
| 6,513,151 B1 | 1/2003 | Erhardt et al. | |
| 6,526,164 B1 | 2/2003 | Mansfield et al. | |
| 6,529,621 B1 | 3/2003 | Glasser et al. | |
| 6,535,628 B2 | 3/2003 | Smargiassi et al. | |
| 6,539,106 B1 | 3/2003 | Gallarda et al. | |
| 6,569,691 B1 | 5/2003 | Jastrzebski et al. | |
| 6,581,193 B1 | 6/2003 | McGhee et al. | |
| 6,593,748 B1 | 7/2003 | Halliyal et al. | |
| 6,597,193 B2 | 7/2003 | Lagowski et al. | |
| 6,602,728 B1 | 8/2003 | Liebmann et al. | |
| 6,608,681 B2 | 8/2003 | Tanaka et al. | |
| 6,614,520 B1 | 9/2003 | Baraket et al. | |
| 6,631,511 B2 | 10/2003 | Haffner | |
| 6,636,301 B1 | 10/2003 | Kvamme et al. | |
| 6,642,066 B1 | 11/2003 | Halliyal et al. | |
| 6,658,640 B2 | 12/2003 | Weed | |
| 6,665,065 B1 | 12/2003 | Phan et al. | |
| 6,670,082 B2 | 12/2003 | Liu et al. | |
| 6,680,621 B2 | 1/2004 | Savtchouk et al. | |
| 6,691,052 B1 | 2/2004 | Maurer | |
| 6,701,004 B1 | 3/2004 | Shykind et al. | |
| 6,718,526 B1 | 4/2004 | Eldredge et al. | |
| 6,721,695 B1 | 4/2004 | Chen et al. | |
| 6,734,696 B2 | 5/2004 | Horner et al. | |
| 6,738,954 B1 | 5/2004 | Allen et al. | |
| 6,751,519 B1 | 6/2004 | Satya et al. | |
| 6,753,954 B2 | 6/2004 | Chen | |
| 6,757,645 B2 | 6/2004 | Chang | |
| 6,759,655 B2 | 7/2004 | Nara et al. | |
| 6,771,806 B1 | 8/2004 | Satya et al. | |
| 6,775,818 B2 | 8/2004 | Taravade et al. | |
| 6,777,147 B1 | 8/2004 | Fonseca et al. | |
| 6,777,676 B1 | 8/2004 | Wang et al. | |
| 6,778,695 B1 | 8/2004 | Schellenberg et al. | |

| | | | | | |
|---|---|---|---|---|---|
| 6,779,159 B2 | 8/2004 | Yokoyama et al. | 2002/0033449 A1 | 3/2002 | Nakasuji et al. |
| 6,784,446 B1 | 8/2004 | Phan et al. | 2002/0035461 A1 | 3/2002 | Chang et al. |
| 6,788,400 B2 | 9/2004 | Chen | 2002/0035641 A1 | 3/2002 | Kurose |
| 6,789,032 B2 | 9/2004 | Barbour et al. | 2002/0035717 A1 | 3/2002 | Matsuoka |
| 6,803,554 B2 | 10/2004 | Ye et al. | 2002/0088951 A1 | 7/2002 | Chen |
| 6,806,456 B1 | 10/2004 | Ye et al. | 2002/0090746 A1 | 7/2002 | Xu et al. |
| 6,807,503 B2 | 10/2004 | Ye et al. | 2002/0134936 A1 | 9/2002 | Matsui et al. |
| 6,813,572 B2 | 11/2004 | Satya et al. | 2002/0144230 A1 | 10/2002 | Rittman |
| 6,820,028 B2 | 11/2004 | Ye et al. | 2002/0145734 A1 | 10/2002 | Watkins et al. |
| 6,828,542 B2 | 12/2004 | Ye et al. | 2002/0164065 A1 | 11/2002 | Cai et al. |
| 6,842,225 B1 | 1/2005 | Irie | 2002/0176096 A1 | 11/2002 | Sentoku et al. |
| 6,859,746 B1 | 2/2005 | Stirton | 2002/0181756 A1 | 12/2002 | Shibuya et al. |
| 6,879,403 B2 | 4/2005 | Freifeld | 2002/0186878 A1 | 12/2002 | Hoon et al. |
| 6,879,924 B2 | 4/2005 | Ye et al. | 2002/0192578 A1 | 12/2002 | Tanaka et al. |
| 6,882,745 B2 | 4/2005 | Brankner et al. | 2003/0014146 A1 | 1/2003 | Fujii |
| 6,884,984 B2 | 4/2005 | Ye et al. | 2003/0017664 A1 | 1/2003 | Pnueli et al. |
| 6,886,153 B1 | 4/2005 | Bevis | 2003/0022401 A1 | 1/2003 | Hamamatsu et al. |
| 6,892,156 B2 | 5/2005 | Ye et al. | 2003/0033046 A1 | 2/2003 | Yoshitake et al. |
| 6,902,855 B2 | 6/2005 | Peterson et al. | 2003/0048458 A1 | 3/2003 | Mieher |
| 6,906,305 B2 | 6/2005 | Pease et al. | 2003/0048939 A1 | 3/2003 | Lehman |
| 6,918,101 B1 | 7/2005 | Satya et al. | 2003/0057971 A1 | 3/2003 | Nishiyama et al. |
| 6,919,957 B2 * | 7/2005 | Nikoonahad et al. ...... 356/237.2 | 2003/0086081 A1 | 5/2003 | Lehman |
| 6,937,753 B1 | 8/2005 | O'Dell et al. | 2003/0094572 A1 | 5/2003 | Matsui et al. |
| 6,948,141 B1 | 9/2005 | Satya et al. | 2003/0098805 A1 | 5/2003 | Bizjak |
| 6,959,255 B2 | 10/2005 | Ye et al. | 2003/0128870 A1 | 7/2003 | Pease et al. |
| 6,966,047 B1 | 11/2005 | Glasser | 2003/0138138 A1 | 7/2003 | Vacca et al. |
| 6,969,837 B2 | 11/2005 | Ye et al. | 2003/0138978 A1 | 7/2003 | Tanaka et al. |
| 6,969,864 B2 | 11/2005 | Ye et al. | 2003/0169916 A1 | 9/2003 | Hayashi et al. |
| 6,983,060 B1 | 1/2006 | Martinent-Catalot et al. | 2003/0192015 A1 | 10/2003 | Liu |
| 6,988,045 B2 | 1/2006 | Purdy | 2003/0207475 A1 | 11/2003 | Nakasuji et al. |
| 7,003,755 B2 | 2/2006 | Pang et al. | 2003/0223639 A1 | 12/2003 | Shlain et al. |
| 7,003,758 B2 | 2/2006 | Ye et al. | 2003/0226951 A1 | 12/2003 | Ye et al. |
| 7,012,438 B1 | 3/2006 | Miller et al. | 2003/0228714 A1 | 12/2003 | Smith |
| 7,026,615 B2 | 4/2006 | Takane | 2003/0229410 A1 | 12/2003 | Smith |
| 7,027,143 B1 | 4/2006 | Stokowski et al. | 2003/0229412 A1 | 12/2003 | White |
| 7,030,966 B2 | 4/2006 | Hansen | 2003/0229868 A1 | 12/2003 | White |
| 7,030,997 B2 | 4/2006 | Neureuther et al. | 2003/0229875 A1 | 12/2003 | Smith |
| 7,053,355 B2 | 5/2006 | Ye et al. | 2003/0229880 A1 | 12/2003 | White |
| 7,061,625 B1 | 6/2006 | Hwang | 2003/0229881 A1 | 12/2003 | White |
| 7,071,833 B2 | 7/2006 | Nagano et al. | 2003/0237064 A1 | 12/2003 | White et al. |
| 7,103,484 B1 | 9/2006 | Shi et al. | 2004/0030430 A1 | 2/2004 | Matsuoka |
| 7,106,895 B1 | 9/2006 | Goldberg et al. | 2004/0032908 A1 | 2/2004 | Hagai et al. |
| 7,107,517 B1 | 9/2006 | Suzuki et al. | 2004/0049722 A1 | 3/2004 | Matsushita |
| 7,107,571 B2 | 9/2006 | Chang et al. | 2004/0052411 A1 | 3/2004 | Qian et al. |
| 7,111,277 B2 | 9/2006 | Ye et al. | 2004/0057611 A1 | 3/2004 | Lee |
| 7,114,143 B2 | 9/2006 | Hanson et al. | 2004/0091142 A1 | 5/2004 | Peterson et al. |
| 7,114,145 B2 | 9/2006 | Ye et al. | 2004/0094762 A1 | 5/2004 | Hess et al. |
| 7,117,477 B2 | 10/2006 | Ye et al. | 2004/0098216 A1 | 5/2004 | Ye et al. |
| 7,117,478 B2 | 10/2006 | Ye et al. | 2004/0102934 A1 | 5/2004 | Chang |
| 7,120,285 B1 | 10/2006 | Spence | 2004/0107412 A1 | 6/2004 | Pack et al. |
| 7,120,895 B2 | 10/2006 | Ye et al. | 2004/0119036 A1 | 6/2004 | Ye et al. |
| 7,123,356 B1 | 10/2006 | Stokowski | 2004/0120569 A1 | 6/2004 | Hung et al. |
| 7,124,386 B2 | 10/2006 | Smith | 2004/0133369 A1 | 7/2004 | Pack et al. |
| 7,133,548 B2 | 11/2006 | Kenan et al. | 2004/0174506 A1 | 9/2004 | Smith |
| 7,135,344 B2 | 11/2006 | Nehmadi | 2004/0223639 A1 | 11/2004 | Sato et al. |
| 7,136,143 B2 | 11/2006 | Smith | 2004/0228515 A1 | 11/2004 | Okabe et al. |
| 7,152,215 B2 | 12/2006 | Smith | 2004/0234120 A1 | 11/2004 | Honda et al. |
| 7,162,071 B2 | 1/2007 | Hung et al. | 2004/0243320 A1 | 12/2004 | Chang et al. |
| 7,171,334 B2 | 1/2007 | Gassner | 2004/0254752 A1 | 12/2004 | Wisniewski et al. |
| 7,174,520 B2 | 2/2007 | White | 2005/0004774 A1 | 1/2005 | Volk et al. |
| 7,194,709 B2 | 3/2007 | Brankner | 2005/0008218 A1 | 1/2005 | O'Dell et al. |
| 7,207,017 B1 | 4/2007 | Tabery et al. | 2005/0010890 A1 | 1/2005 | Nehmadi et al. |
| 7,231,628 B2 | 6/2007 | Pack et al. | 2005/0062962 A1 | 3/2005 | Fairley |
| 7,236,847 B2 | 6/2007 | Marella | 2005/0117796 A1 | 6/2005 | Matsui |
| 7,379,175 B1 | 5/2008 | Stokowski et al. | 2005/0132306 A1 | 6/2005 | Smith |
| 7,383,156 B2 | 6/2008 | Matsusita et al. | 2005/0141764 A1 | 6/2005 | Tohyama et al. |
| 7,386,839 B1 | 6/2008 | Golender et al. | 2005/0166174 A1 | 7/2005 | Ye et al. |
| 7,418,124 B2 | 8/2008 | Peterson et al. | 2005/0184252 A1 | 8/2005 | Ogawa et al. |
| 7,424,145 B2 | 9/2008 | Horie et al. | 2005/0190957 A1 | 9/2005 | Cai et al. |
| 7,676,077 B2 | 3/2010 | Kulkarni et al. | 2005/0198602 A1 | 9/2005 | Brankner |
| 7,683,319 B2 * | 3/2010 | Makino et al. ............ 250/310 | 2006/0000964 A1 | 1/2006 | Ye et al. |
| 7,738,093 B2 | 6/2010 | Alles et al. | 2006/0036979 A1 | 2/2006 | Zurbrick et al. |
| 7,739,064 B1 | 6/2010 | Ryker et al. | 2006/0048089 A1 | 3/2006 | Schwarzband |
| 2001/0017694 A1 | 8/2001 | Oomori et al. | 2006/0051682 A1 | 3/2006 | Hess et al. |
| 2001/0019625 A1 | 9/2001 | Kenan et al. | 2006/0062445 A1 | 3/2006 | Verma et al. |
| 2001/0022858 A1 | 9/2001 | Komiya et al. | 2006/0082763 A1 | 4/2006 | The et al. |
| 2001/0043735 A1 | 11/2001 | Smargiassi et al. | 2006/0159333 A1 | 7/2006 | Ishikawa |
| 2002/0019729 A1 | 2/2002 | Chang et al. | 2006/0161452 A1 | 7/2006 | Hess et al. |
| 2002/0026626 A1 | 2/2002 | Randall et al. | 2006/0193506 A1 | 8/2006 | Dorphan et al. |

| | | | |
|---|---|---|---|
| 2006/0193507 | A1 | 8/2006 | Sali et al. |
| 2006/0236294 | A1 | 10/2006 | Saidin |
| 2006/0236297 | A1 | 10/2006 | Melvin et al. |
| 2006/0239536 | A1 | 10/2006 | Shibuya et al. |
| 2006/0265145 | A1 | 11/2006 | Huet et al. |
| 2006/0266243 | A1 | 11/2006 | Percin et al. |
| 2006/0269120 | A1 | 11/2006 | Nehmadi et al. |
| 2006/0273242 | A1 | 12/2006 | Hunsche et al. |
| 2006/0273266 | A1 | 12/2006 | Preil et al. |
| 2006/0291714 | A1 | 12/2006 | Wu et al. |
| 2006/0292463 | A1 | 12/2006 | Best et al. |
| 2007/0002322 | A1 | 1/2007 | Borodovsky et al. |
| 2007/0013901 | A1 | 1/2007 | Kim et al. |
| 2007/0019171 | A1 | 1/2007 | Smith |
| 2007/0031745 | A1 | 2/2007 | Ye et al. |
| 2007/0032896 | A1 | 2/2007 | Ye et al. |
| 2007/0035322 | A1 | 2/2007 | Kang et al. |
| 2007/0035712 | A1 | 2/2007 | Gassner et al. |
| 2007/0035728 | A1 | 2/2007 | Kekare et al. |
| 2007/0052963 | A1 | 3/2007 | Orbon |
| 2007/0064995 | A1 | 3/2007 | Oaki et al. |
| 2007/0156379 | A1 | 7/2007 | Kulkarni et al. |
| 2007/0230770 | A1 | 10/2007 | Kulkarni et al. |
| 2007/0248257 | A1 | 10/2007 | Bruce et al. |
| 2007/0280527 | A1 | 12/2007 | Almogy et al. |
| 2007/0288219 | A1 | 12/2007 | Zafar et al. |
| 2008/0049994 | A1 | 2/2008 | Rognin et al. |
| 2008/0072207 | A1 | 3/2008 | Verma et al. |
| 2008/0081385 | A1 | 4/2008 | Marella et al. |
| 2008/0295047 | A1 | 11/2008 | Nehmadi et al. |
| 2008/0304056 | A1 | 12/2008 | Alles et al. |
| 2009/0016595 | A1 | 1/2009 | Peterson et al. |
| 2009/0024967 | A1 | 1/2009 | Su et al. |
| 2009/0041332 | A1 | 2/2009 | Bhaskar et al. |
| 2009/0055783 | A1 | 2/2009 | Florence et al. |
| 2009/0210183 | A1 | 8/2009 | Rajski et al. |

FOREIGN PATENT DOCUMENTS

| | | |
|---|---|---|
| EP | 0370322 | 5/1990 |
| EP | 1061358 | 12/2000 |
| EP | 1061571 | 12/2000 |
| EP | 1065567 | 1/2001 |
| EP | 1066925 | 1/2001 |
| EP | 1069609 | 1/2001 |
| EP | 1093017 | 4/2001 |
| EP | 1480034 | 11/2004 |
| EP | 1696270 | 8/2006 |
| JP | 2002-071575 | 3/2002 |
| JP | 2002-365235 | 12/2002 |
| JP | 2003-215060 | 7/2003 |
| JP | 2004-045066 | 2/2004 |
| JP | 2005-283326 | 10/2005 |
| KR | 10-2001-0037026 | 5/2001 |
| KR | 10-2001-0101697 | 11/2001 |
| KR | 1020030055848 | 7/2003 |
| KR | 10-2005-0092053 | 9/2005 |
| KR | 10-2006-0075691 | 7/2006 |
| WO | WO 98/57358 | 12/1998 |
| WO | WO 99/22310 | 5/1999 |
| WO | WO 99/25004 | 5/1999 |
| WO | WO 99/38002 | 7/1999 |
| WO | WO 99/41434 | 8/1999 |
| WO | WO 99/59200 | 11/1999 |
| WO | WO 00/03234 | 1/2000 |
| WO | WO 00/36525 | 6/2000 |
| WO | WO 00/55799 | 9/2000 |
| WO | WO 00/68884 | 11/2000 |
| WO | WO 00/70332 | 11/2000 |
| WO | WO 01/09566 | 2/2001 |
| WO | WO 01/40145 | 6/2001 |
| WO | WO 03/104921 | 12/2003 |
| WO | WO 2004/027684 | 4/2004 |
| WO | WO 2006/063268 | 6/2006 |
| WO | 2010/093733 | 8/2010 |

OTHER PUBLICATIONS

O'Gorman et al., "Subpixel Registration Using a Concentric Ring Fiducial," Proceedings of the International Conference on Pattern Recognition, vol. ii, Jun. 16, 1990, pp. 249-253.

U.S. Appl. No. 11/830,485, filed Jul. 2007, Kulkarni et al.

U.S. Appl. No. 11/950,961, filed Dec. 2007, Fouquet et al.

U.S. Appl. No. 12/102,343, filed Apr. 2008, Chen et al.

Svidenko et al. "Dynamic Defect-Limited Yield Prediction by Criticality Factor," ISSM Paper YE-O-157, 2007.

Barty et al., "Aerial Image Microscopes for the inspection of defects in EUV masks," Proceedings of SPIE, vol. 4889, 2002, pp. 1073-1084.

Budd et al., "A New Mask Evaluation Tool, the Microlithography Simulation Microscope Aerial Image Measurement System," SPIE vol. 2197, 1994, pp. 530-540.

Cai et al., "Enhanced Dispositioning of Reticle Defects Using the Virtual Stepper With Automoated Defect Severity Scoring," Proceedings of the SPIE, vol. 4409, Jan. 2001, pp. 467-478.

Comizzoli, "Uses of Corono Discharges in the Semiconfuctor Industry," J. Electrochem. Soc., 1987, pp. 424-429.

Contactless Electrical Equivalent Oxide Thickness Measurement, IBM Technical Disclosure Bulletin, vol. 29, No. 10, 1987, pp. 4622-4623.

Contactless Photovoltage vs. Bias Method for Determining Flat-Band Voltage, IBM Technical Disclosure Bulletin, vol. 32, vol. 9A, 1990, pp. 14-17.

Cosway et al., "Manufacturing Implementation of Corona Oxide Silicon (COS) Systems for Diffusion Furnace Contamination Monitoring," 1997 IEEE/SEMI Advanced Semiconductor Manufacturing Conference, pp. 98-102.

Diebold et al., "Characterization and produiction metrology of thin transistor gate oxide films," Materials Science in Semiconductor Processing 2, 1999, pp. 103-147.

Garcia et al., "New Die to Database Inspection Algorithm for Inspection of 90-nm Node Reticles," Proceedings of SPIE, vol. 5130, 2003, pp. 364-374.

Granik et al., "Sub-resolution process windows and yield estimation technique based on detailed full-chip CD simulation," Mentor Graphics, Sep. 2000, 5 pages.

Hess et al., "A Novel Approach: High Resolution Inspection with Wafer Plane Defect Detection," Proceedings of SPIE—International Society for Optical Engineering; Photomask and Next-Generation Lithography Mask Technology 2008, vol. 7028, 2008.

Huang et al., "Process Window Impact of Progressive Mask Defects, Its Inspection and Disposition Techniques (go/no-go criteria) Via a Lithographic Detector," Proceedings of SPIE—The International Society for Optical Engineering; 25th Annual Bacus Symposium on Photomask Technology 2005, vol. 5992, No. 1, 2005, p. 6.

Hung et al., Metrology Study of Sub 20 Angstrom oxynitride by Corona-Oxide-Silicon (COS) and Conventional C-V Approaches, 2002, Mat. Res. Soc. Symp. Proc., vol. 716, pp. 119-124.

International Search Report and Written Opinion for PCT Appln. No. PCT/US06/61112 dated Sep. 25, 2008.

International Search Report and Written Opinion for PCT Appln. No. PCT/US06/61113 dated Jul. 16, 2008.

International Search Report and Written Opinion for PCT Appln. No. PCT/US08/050397 dated Jul. 11, 2008.

International Search Report and Written Opinion for PCT/US2008/062873 mailed Aug. 12, 2008.

International Search Report for PCT/US2008/62875 mailed Sep. 10, 2008.

International Search Report and Written Opinion for PCT Appln. No. PCT/US2008/063008 dated Aug. 18, 2008.

International Search Report for PCT/US2003/21907 mailed Jun. 7, 2004.

International Search Report for PCT/US2004/040733 mailed Dec. 23, 2005.

Karklin et al., "Automatic Defect Severity Scoring for 193 nm Reticle Defect Inspection," Proceedings of SPIE—The International Society for Optical Engineering, 2001, vol. 4346, No. 2, pp. 898-906.

Lu et al., "Application of Simulation Based Defect Printability Analysis for Mask Qualification Control," Proceedings of SPIE, vol. 5038, 2003, pp. 33-40.

Martino et al., "Application of the Aerial Image Measurement System (AIMS(TM)) to the Analysis of Binary Mask Imaging and Resolution Enhancement Techniques," SPIE vol. 2197, 1994, pp. 573-584.

Miller, "A New Approach for Measuring Oxide Thickness," Semiconductor International, Jul. 1995, pp. 147-148.

Nagpal et al., "Wafer Plane Inspection for Advanced Reticle Defects," Proceedings of SPIE—The International Society for Optical Engineering; Photomask and Next-Generation Lithography Mask Technology. vol. 7028, 2008.

Numerical Recipes in C. The Art of Scientific Computing, 2nd Ed.,© Cambridge University Press 1988, 1992, p. 683.

Otsu, "A Threshold Selection Method from Gray-Level Histograms," IEEE Transactions on Systems, Man, and Cybernetics, vol. SMC-9, No. 1, Jan. 1979, pp. 62-66.

Pang et al., "Simulation-based Defect Printability Analysis on Alternating Phase Shifting Masks for 193 nm Lithography," Proceedings of SPIE, vol. 4889, 2002, pp. 947-954.

Pettibone et al., "Wafer Printability Simulation Accuracy Based on UV Optical Inspection Images of Reticle Defects," Proceedings of SPIE—The International Society for Optical Engineering 1999 Society of Photo-Optical Instrumentation Engineers, vol. 3677, No. II, 1999, pp. 711-720.

Phan et al., "Comparison of Binary Mask Defect Printability Analysis Using Virtual Stepper System and Aerial Image Microscope System," Proceedings of SPIE—The International Society for Optical Engineering 1999 Society of Photo-Optical Instrumentation Engineers, vol. 3873, 1999, pp. 681-692.

Sahouria et al., "Full-chip Process Simulation for Silicon DRC," Mentor Graphics, Mar. 2000, 6 pages.

Schroder et al., Corono-Oxide-Semiconductor Device Characterization, 1998, Solid-State Electronics, vol. 42, No. 4, pp. 505-512.

Schroder, "Surface voltage and surface photovoltage; history, theory and applications," Measurement Science and Technology, vol. 12, 2001, pp. R16-R31.

Schroder, Contactless Surface Charge Semiconductor Characterization, Apr. 2002, Materials Science and Engineering B, vol. 91-92, pp. 196-228.

Schurz et al., "Simulation Study of Reticle Enhancement Technology Applications for 157 nm Lithography," SPIE vol. 4562, 2002, pp. 902-913.

U.S. Appl. No. 10/677,445 (Horner et al.) entitled Methods for Non-Contacting Differential Voltage Measurements filed Oct. 2, 2003.

U.S. Appl. No. 11/139,151 (Volk et al.) entitled Methods and Systems for Detecting Changes in Reticle Defectivity Over Time filed May 27, 2005.

U.S. Appl. No. 60/418,887 (Su et al.) entitled Methods and Systems for Inspecting Reticles Using Aerial Imaging and Die-To-Database Detection filed Oct. 15, 2002.

U.S. Appl. No. 60/419,028 (Stokowski et al.) entitled Methods and Systems for Inspecting Reticles Using Aerial Imaging At Off-Stepper Wavelengths filed Oct. 15, 2002.

U.S. Appl. No. 60/485,233 (Peterson et al.) entitled Qualifying Patterns, Patterning Processes, or Patterning Apparatus in the Fabrication of Microlithographic Patterns filed Jul. 7, 2003.

U.S. Appl. No. 60/526,881 (Hess et al,) entitled Designer Intent filed Dec. 4, 2003.

U.S. Appl. No. 60/681,095 (Nehmadi et al.) entitled Methods in Mask and Process Qualification filed May 13, 2005.

U.S. Appl. No. 60/684,360 (Nehmadi et al.) entitled Design-Based Inspection filed May 24, 2005.

Verkuil et al., "A Contactless Alternative to MOS Charge Measurements by Means of a Corona-Oxide-Semiconductor (COS) Technique,"Electrochem. Soc. Extended Abstracts, 1988, vol. 88-1, No. 169, pp. 261-262.

Verkuil, "Rapid Contactless Method for Measuring Fixed Oxide Charge ASsociated with SIlicon Processing," IBM Technical Disclosure Bulletin, vol. 24, No. 6, 1981, pp. 3048-3053.

Volk et al. "Investigation of Reticle Defect Formation at DUV Lithography," 2002, BACUS Symposium on Photomask Technology.

Volk et al. "Investigation of Reticle Defect Formation at DUV Lithography," 2003, IEEE/SEMI Advanced Manufacturing Conference, pp. 29-35.

Weinberg, "Tunneling of Electrons from Si into Thermally Grown SiO2," Solid-State Electronics, 1977, vol. 20, pp. 11-18.

Weinzierl et al., "Non-Contact Corona-Based Process Control Measurements: Where We've Been, Where We're Headed," Electrochemical Society Proceedings, Oct. 1999, vol. 99-16, pp. 342-350.

Yan et al., "Printability of Pellicle Defects in DUV 0.5 um Lithography," SPIE vol. 1604, 1991, pp. 106-117.

International Search Report for PCT/US2008/070647 mailed Dec. 16, 2008.

International Search Report and Written Opinion for PCT/US2008/073706 mailed Jan. 29, 2009.

International Search Report and Written Opinion for PCT/US2008/072636 mailed Jan. 29, 2009.

Tang et al., "Analyzing Volume Diagnosis Results with Statistical Learning for Yield Improvement" 12th IEEE European Test Symposium, Freiburg 2007, IEEE European, May 20-24, 2007, pp. 145-150.

Huang et al., "Using Design Based Binning to Improve Defect Excursion Control for 45nm Production," IEEE, International Symposium on Semiconductor Manufacturing, Oct. 2007, pp. 1-3.

Sato et al., "Defect Criticality Index (DCI): A new methodology to significantly improve DOI sampling rate in a 45nm production environment," Metrology, Inspection, and Process Control for Microlithography XXII, Proc. Of SPIE vol. 6922, 692213 (2008), pp. 1-9.

U.S. Appl. No. 60/418,994, filed Oct. 2002, Stokowski.
U.S. Appl. No. 60/451,707, filed Mar. 2003, Howard.
U.S. Appl. No. 60/609,670, filed Sep. 2004, Preil.
U.S. Appl. No. 60/738,290, filed Nov. 2005, Kulkarni.
U.S. Appl. No. 60/772,418, filed Feb. 2006, Kirk et al.
U.S. Appl. No. 10/679,617, filed Oct. 2003, Stokowski.
U.S. Appl. No. 10/778,752, filed Feb. 2004, Mack.
U.S. Appl. No. 10/793,599, filed Mar. 2004, Howard.
U.S. Appl. No. 11/154,310, filed Jun. 2005, Verma et al.
U.S. Appl. No. 11/300,172, filed Dec. 2005, Lin.
U.S. Appl. No. 11/673,150, filed Feb. 2007, Kirk et al.
U.S. Appl. No. 11/837,208, filed Aug. 2007, Park.
U.S. Appl. No. 11/960,157, filed Dec. 2007, Kulkarni et al.
U.S. Appl. No. 11/970,294, filed Jan. 2008, Park et al.

Dirksen et al., "Impact of high order aberrations on the performance of the aberration monitor," Proc. Of SPIE vol. 4000, Mar. 2000, pp. 9-17.

Dirksen et al., "Novel aberration monitor for optical lithography," Proc. Of SPIE vol. 3679, Jul. 1999, pp. 77-86.

Lo et al., "Identifying Process Window Marginalities of Reticle Designs for 0.15/0.13 μm Technologies," Proceedings of SPIE vol. 5130, 2003, pp. 829-837.

Lorusso et al. "Advanced DFM Applns. Using design-based metrology on CDSEM," SPIE vol. 6152, Mar. 27, 2006.

Mack, "Lithographic Simulation: A Review," Proceedings of SPIE vol. 4440, 2001, pp. 59-72.

Svidenko et al. "Dynamic Defect-Limited Yield Prediction by Criticality Factor," ISSM Paper: YE-O-157, 2007.

Volk et al., "Investigation of Smart Inspection of Critical Layer Reticles using Additional Designer Data to Determine Defect Significance," Proceeings of SPIE vol. 5256, 2003, pp. 489-499.

Allan et al., "Critical Area Extraction for Soft Fault Estimation," IEEE Transactions on Semiconductor Manufacturing, vol. 11, No. 1, Feb. 1998.

* cited by examiner

METHODS AND SYSTEMS FOR USING ELECTRICAL INFORMATION FOR A DEVICE BEING FABRICATED ON A WAFER TO PERFORM ONE OR MORE DEFECT-RELATED FUNCTIONS

PRIORITY CLAIM

This application claims priority to U.S. Provisional Application No. 60/883,617 entitled "Methods and Systems for Using Device Information to Perform One or More Defect-Related Functions," filed Jan. 5, 2007, which is incorporated by reference as if fully set forth herein.

BACKGROUND OF THE INVENTION

1. Field of the Invention

The present invention generally relates to methods and systems for using electrical information for a device being fabricated on a wafer to perform one or more defect-related functions. Certain embodiments relate to a computer-implemented method that includes using critical path information, electrical information, electrical design information, or some combination thereof for a device being fabricated on a wafer to perform one or more defect-related functions.

2. Description of the Related Art

The following description and examples are not admitted to be prior art by virtue of their inclusion in this section.

An integrated circuit (IC) design may be developed using a method or system such as electronic design automation (EDA), computer aided design (CAD), and other IC design software. Such methods and systems may be used to generate a circuit pattern database from the IC design. The circuit pattern database includes data representing a plurality of layouts for various layers of the IC. Data in the circuit pattern database may be used to determine layouts for a plurality of reticles. A layout of a reticle generally includes a plurality of polygons that define features in a pattern on the reticle. Each reticle is used to fabricate one of the various layers of the IC. The layers of the IC may include, for example, a junction pattern in a semiconductor substrate, a gate dielectric pattern, a gate electrode pattern, a contact pattern in an interlevel dielectric, and an interconnect pattern on a metallization layer.

A semiconductor device design is verified by different procedures before production of ICs. For example, the semiconductor device design is checked by software simulation to verify that all features will be printed correctly after lithography in manufacturing. Such checking commonly includes steps such as design rule checking (DRC), optical rule checking (ORC), and more sophisticated software-based verification approaches that include process simulation calibrated to a specific fab and process. The output of the physical design verification steps can be used to identify a potentially large number of critical points, sometimes referred to as "hot spots," in the design.

Fabricating semiconductor devices such as logic and memory devices typically includes processing a substrate such as a semiconductor wafer using a large number of semiconductor fabrication processes to form various features and multiple levels of the semiconductor devices. For example, lithography is a semiconductor fabrication process that involves transferring a pattern from a reticle to a resist arranged on a semiconductor wafer. Additional examples of semiconductor fabrication processes include, but are not limited to, chemical-mechanical polishing (CMP), etch, deposition, and ion implantation. Multiple semiconductor devices may be fabricated in an arrangement on a single semiconductor wafer and then separated into individual semiconductor devices.

Inspection processes are used at various steps during a semiconductor manufacturing process to detect defects on wafers to promote higher yield in the manufacturing process and thus higher profits. Inspection has always been an important part of fabricating semiconductor devices such as ICs. However, as the dimensions of semiconductor devices decrease, inspection becomes even more important to the successful manufacture of acceptable semiconductor devices because smaller defects can cause the devices to fail. For instance, as the dimensions of semiconductor devices decrease, detection of defects of decreasing size has become necessary since even relatively small defects may cause unwanted aberrations in the semiconductor devices.

Another important part of manufacturing yield control is determining the cause of defects on wafers such that the cause of the defects can be corrected to thereby reduce the number of defects on other wafers. Often, determining the cause of defects involves identifying the defect type and other attributes of the defects such as size, shape, composition, etc. Since inspection typically only involves detecting defects on wafers and providing limited information about the defects such as location on the wafers, number of defects on the wafers, and sometimes defect size, defect review is often used to determine more information about individual defects than that which can be determined from inspection results. For instance, a defect review tool may be used to revisit defects detected on a wafer and to examine the defects further in some manner either automatically or manually.

Defect review typically involves generating additional information about defects at a higher resolution using either a high magnification optical system or a scanning electron microscope (SEM). The higher resolution data for the defects generated by defect review is more suitable for determining attributes of the defects such as profile, roughness, more accurate size information, etc Defect analysis may also be performed using a system such as an electron dispersive x-ray spectroscopy (EDS) system. Such defect analysis may be performed to determine information such as composition of the defects. Attributes of the defects determined by inspection, review, analysis, or some combination thereof can be used to identify the type of the defect (i.e., defect classification) and possibly a root cause of the defects. This information can then be used to monitor and alter one or more parameters of one or more semiconductor fabrication processes to reduce or eliminate the defects.

As design rules shrink, however, semiconductor manufacturing processes may be operating closer to the limitations on the performance capability of the processes. In addition, smaller defects can have an impact on the electrical parameters of the device as the design rules shrink, which drives more sensitive inspections. Therefore, as design rules shrink, the population of potentially yield relevant defects detected by inspection grows dramatically, and the population of nuisance defects detected by inspection also increases dramatically. Therefore, more and more defects may be detected on wafers, and correcting the processes to eliminate all of the defects may be difficult and expensive. As such, determining which of the defects actually have an effect on the electrical parameters of the devices and the yield may allow process control methods to be focused on those defects while largely ignoring others. Furthermore, at smaller design rules, process induced failures may, in some cases, tend to be systematic. That is, process induced failures tend to fail at certain design patterns often repeated many times within the design. Elimination of spatially systematic, electrically relevant defects is important because eliminating such defects can have a significant overall impact on yield. Whether or not defects will affect device parameters and yield often cannot be determined from the inspection, review, and analysis processes described above since these processes may not be able to determine the position of the defect with respect to the electrical design.

Some methods and systems for aligning defect information to the electrical design have been developed. For instance, a SEM review system may be used to determine more accurate coordinates of defect locations for a sample of defects, and the defect coordinates reported by the SEM review system may be used to determine locations of defects in the electrical design. Other methods involve aligning inspection care areas (e.g., the areas of the device pattern formed on the wafer in which inspection will be performed) to the physical location of the pattern printed on the wafer. However, currently, the care areas can be aligned to the pattern printed on the wafer with an accuracy of no better than about 2 µm due to system errors and imperfections. For instance, some bright field (BF) inspection systems have coordinate accuracies of about +/−1 µm. In addition, the inspection care areas in currently used methods are relatively large and include many non-critical features as well as desired critical features. In trying to maximize the sensitivity of the inspection system to capture subtle spatially systematic "design-for-manufacturability" (DFM) defects resulting from design and process interdependencies, the system may be overwhelmed by millions of events in non-critical areas such as CMP fill regions. Detecting such nuisance defects is disadvantageous for a number of reasons. For example, these nuisance events need to be filtered out of the inspection results by post-processing of the inspection data. In addition, nuisance event detection limits the ultimate achievable sensitivity of the inspection system for DFM applications. A high rate of nuisance defect data may also overload the run time data processing capacity of the inspection system thereby reducing throughput and/or causing the loss of data.

Accordingly, it would be advantageous to develop methods and systems for using electrical information for a device being fabricated on a wafer to perform one or more defect-related functions that do not have one or more of the disadvantages described above.

SUMMARY OF THE INVENTION

The following description of various embodiments of methods, carrier media, and systems is not to be construed in any way as limiting the subject matter of the appended claims.

One embodiment relates to a computer-implemented method that includes using electrical information for a device being fabricated on a wafer to perform one or more defect-related functions. The one or more defect-related functions include one or more post-mask, defect-related functions.

In one embodiment, the electrical information includes critical path information. In another embodiment, the one or more defect-related functions include determining performance of the device using defect inspection data acquired for the wafer and the electrical information. In another embodiment, the one or more defect-related functions include using the electrical information and defect inspection data acquired for the wafer in real time to determine performance of the device.

In one embodiment, the one or more defect-related functions include determining potential yield impact of defects on the device using defect inspection data acquired for the wafer and the electrical information. In another embodiment, the one or more defect-related functions include using the electrical information and defect inspection data acquired for the wafer in real time to determine potential yield impact of defects on the device. In an additional embodiment, the one or more defect-related functions include determining electrical relevancy of defects detected on the wafer.

In some embodiments, the one or more defect-related functions include determining timing delay of the device due to defects detected on the wafer using defect inspection data acquired for the wafer and the electrical information. In another embodiment, the one or more defect-related functions include using the electrical information and defect inspection data acquired for the wafer in real time to determine timing delay of the device due to defects detected on the wafer.

In one embodiment, the one or more defect-related functions include determining power leakage of the device due to defects detected on the wafer using defect inspection data acquired for the wafer and the electrical information. In another embodiment, the one or more defect-related functions include using the electrical information and defect inspection data acquired for the wafer in real time to determine power leakage of the device due to defects detected on the wafer. In an additional embodiment, the one or more defect-related functions include determining resistance-capacitance variation of the device due to defects detected on the wafer using the electrical information and defect inspection data acquired for the wafer. In a further embodiment, the one or more defect-related functions include using the electrical information and defect inspection data acquired for the wafer in real time to determine resistance-capacitance variation of the device due to defects detected on the wafer.

In one embodiment, the electrical information includes critical path information, and the critical path information is acquired from netlist information for the device. In another embodiment, the one or more defect-related functions include identifying critical defects on the wafer. In an additional embodiment, the one or more defect-related functions include separating defects detected in areas of the wafer corresponding to electrically sensitive areas of the device from other defects detected on the wafer.

In one embodiment, the one or more defect-related functions include identifying one or more inspection areas on the wafer. In another embodiment, the one or more defect-related functions include identifying critical metrology sites on the wafer. In an additional embodiment, the one or more defect-related functions include separating metrology variations measured in areas of the wafer corresponding to electrically sensitive areas of the device from other measured metrology variations. In a further embodiment, the one or more defect-related functions include determining electrical relevancy of metrology data acquired for the wafer.

In one embodiment, the electrical information includes critical path information. In one such embodiment, the critical path information is generated by an electronic design automation tool. In another such embodiment, the one or more defect-related functions include defect sampling in which only defects on the wafer located on or near critical paths in the device are selected for review. In an additional such embodiment, the one or more defect-related functions include overlaying the critical path information with defect inspection data acquired for the wafer and using results of the overlaying step to identify critical defects on the wafer for review.

In one embodiment, the method includes using optimized design data for the device to describe defects detected on the wafer by error budget. In another embodiment, the method includes evaluating optimization of design data for the device by searching the design data for patterns of interest. The patterns of interest include patterns corrected and not corrected by the optimization. In addition, the method includes comparing a failure rate of corrected and non-corrected patterns in the design data for the device.

In one embodiment, the one or more defect-related functions include creating a systematic pareto by critical and non-critical areas of the device to identify critical and non-critical systematic defects on the wafer. In another embodiment, the electrical information includes critical path information. In one such embodiment, the one or more defect-related functions include separating systematic defects detected on the wafer located in critical paths of the device from systematic defects detected on the wafer located in non-critical paths of the device. In another such embodiment, the one or more defect-related functions include separating random defects detected on the wafer located in critical paths of the device from random defects detected on the wafer located in non-critical paths of the device.

In one embodiment, the one or more defect-related functions are performed for defects detected on the wafer by bright field inspection. In another embodiment, the electrical information includes critical path information, and the one or more defect-related functions include using the critical path information to setup a metrology process for the wafer such that changes in critical dimensions of features of the device on the wafer are measured and can be correlated to parametric performance of the device.

In one embodiment, the one or more defect-related functions include inspection of the wafer. In another embodiment, the one or more defect-related functions include defect review of the wafer. In an additional embodiment, the one or more defect-related functions include metrology of the wafer.

In one embodiment, the electrical information includes netlist data. In another embodiment, the electrical information includes netlist data provided to an inspection system used to inspect the wafer. In an additional embodiment, the electrical information includes electrical circuit information.

In some embodiments, the one or more defect-related functions include targeted electron beam-based inspection of the wafer. In another embodiment, the one or more defect-related functions include targeted binning of defects detected by electron beam-based inspection of the wafer.

In one embodiment, the one or more defect-related functions include automatic care area generation for inspection of the wafer. In another embodiment, the one or more defect-related functions include automatic setup of inspection care areas for inspection of the wafer based on circuit electrical function of the device. In an additional embodiment, the one or more defect-related functions include binning defects detected on the wafer based on electrical activity.

In one embodiment, the one or more defect-related functions include binning defects detected on the wafer based on electrical environment of the defects. In another embodiment, the one or more defect-related functions include binning defects detected on the wafer based on connectivity of features of the device such that defects having different connectivity are binned into different groups of defects. In an additional embodiment, the one or more defect-related functions include binning defects detected on the wafer based on connectivity of features of the device such that nuisance defects are binned into a group different than one or more groups of non-nuisance defects. In a further embodiment, the one or more defect-related functions include determining if multiple electrically defective nodes are connected and binning the multiple electrically defective nodes as a single defect if the multiple electrically defective nodes are connected.

In one embodiment, the electrical information includes critical timing paths in the device extracted from netlist data, and the one or more defect-related functions include setup of targeted care areas for inspection of the wafer. In another embodiment, the one or more defect-related functions include using electrical connectivity information for the device to predict voltage contrast gray levels of images acquired during die-to-reference, electron beam-based inspection of the wafer and using the predicted voltage contrast gray levels to match the images to rendered images of design data for the device stored in a data structure. In an additional embodiment, the one or more defect-related functions include rendering images of design data for the device for die-to-reference, electron beam-based inspection of the wafer and storing the rendered images in a data structure.

In one embodiment, the electrical information includes electrical design information for the device being fabricated on the wafer. In another embodiment, the electrical information includes electrical design analysis.

In an additional embodiment, the one or more defect-related functions include assisting defect review of the wafer in real time. In another embodiment, the one or more defect-related functions include assisting defect review of the wafer by assisting in defect classification. In a further embodiment, the one or more defect-related functions include assisting defect review of the wafer by assisting sampling of defects for the defect review.

In one embodiment, the one or more defect-related functions include making one or more decisions in real time during defect review of a defect location on the wafer. In one such embodiment, the defect location is determined based on inspection of a reticle used to print a portion of the device on the wafer. In another such embodiment, the defect location is determined based on design analysis of the device performed to determine critical hot spots for defect detection or monitoring.

In another embodiment, the one or more defect-related functions include determining, in real time during defect review of a defect location on the wafer, if a defect at the defect location is electrically relevant to the device. In another embodiment, the one or more defect-related functions include determining, in real time during defect review of a defect location on the wafer, if additional spot inspections of other parts of the device in the same electrical path as a defect at the defect location are to be performed to assist in determining electrical relevance of the defect. In an additional embodiment, the one or more defect-related functions include determining, in real time during defect review of a defect location on the wafer, if additional spot inspections of other parts of the device in the same electrical path and layer as a defect at the defect location are to be performed to assist in determining electrical relevance of the defect. In a further embodiment, the one or more defect-related functions include determining, in real time during defect review of a defect location on the wafer, if additional spot inspections of other parts of the device in the same electrical path as a defect at the defect location and on layers other than a layer associated with the defect are to be performed to assist in determining electrical relevance of the defect.

In one embodiment, the one or more defect-related functions include binning, in real time during defect review, reviewed defects on the wafer in a pareto chart based on the electrical information. In one such embodiment, the electrical information includes analysis of the design, and the one or more defect-related functions include determining, in real time during the defect review, an electrical-based ranking of an effect on yield of one or more of the reviewed defects.

In one embodiment, the one or more defect-related functions include defect classification. In another embodiment, the one or more defect-related functions include identifying electrically critical hot spots in the device. In an additional embodiment, the one or more defect-related functions include identifying electrically critical hot spots in the device using information from a tool configured to define a process window for fabrication of the device on the wafer. In one such embodiment, the electrically critical hot spots include locations at an edge of the process window for the device and critical to electrical performance of the device. In a further embodiment, the one or more defect-related functions include identifying electrically critical hot spots in the device and selecting the electrically critical hot spots for inspection, monitoring, or some combination thereof during defect review performed on the wafer.

In one embodiment, the method includes generating the electrical information by processing design data for the device, and the design data includes physical layout information, three-dimensional structure information, netlist information, or some combination thereof. In one such embodiment, the one or more defect-related functions include determining a classification or ranking in real time for a defect on the wafer reviewed by a defect review tool. In another such embodiment, the one or more defect-related functions include using the electrical information and defect information generated by a defect review toot to determine electrical effects on the device due to defects detected on the wafer and using the electrical effects to determine a classification or ranking for the defects.

In one embodiment, prior to defect review, the method includes generating the electrical information using design data for the device to determine locations of the most critical areas of the device in terms of electrical performance and storing the locations in a storage medium accessible by a review tool. In one such embodiment, the one or more defect-related functions include using the locations to monitor the locations for defectivity.

In one embodiment, the one or more defect-related functions include using electrical critical dimension margins for defect classification. In another embodiment, the one or more defect-related functions include real time defect classification based on electrical performance effects on the device due to defects detected on the wafer and sampling the defects for review based on electrical design data. In an additional embodiment, the one or more defect-related functions include determining an effect of a defect on the wafer on electrical performance of the device.

In one embodiment, the one or more defect-related functions include using electrically critical hot spots in the device to perform defect monitoring. In another embodiment, the one or more defect-related functions include using the electrical information to determine additional device sampling based on a defect detected on the wafer.

In one embodiment, the one or more defect-related functions include, during inspection of the wafer, classifying defects detected on the wafer into different memory-specific failure modes. In another embodiment, the one or more defect-related functions include classifying defects detected on the wafer into different memory-specific failure modes. In one such embodiment, the method includes altering a memory redundancy design optimization strategy based on results of classifying the defects. In another such embodiment, the method includes determining testing to be performed on the wafer based on results of classifying the defects.

In one embodiment, the one or more defect-related functions include inline memory failure mode classification performed based on defect inspection data and design context surrounding defects detected on the wafer. In another embodiment, the one or more defect-related functions include inline memory failure mode classification, and the inline memory failure mode classification includes registering patterns of interest in the device, performing defect inspection, retrieving GDS clips for every defect detected by the defect inspection, classifying the defects based on GDS matching with known patterns of interest, and based on defect location and defect size, classifying the defects into different memory failure modes.

In one embodiment, the one or more defect-related functions include separating bit failure from word-line or bit-line failure using patterns of interest. In another embodiment, the one or more defect-related functions include separating single bit failure from double-bit failure based on defect size. In an additional embodiment, the one or more defect-related functions include inline memory failure mode classification, and the inline memory failure mode classification includes associating a defect to a layer of the device and location of cells in the device to determine the failure mode of the defect.

Each of the steps of each of the embodiments of the method described above may be further performed as described herein. In addition, each of the embodiments of the method described above may include any other step(s) of any other method(s) described herein. Furthermore, each of the embodiments of the method described above may be performed by any of the systems described herein.

Another embodiment relates to a carrier medium that includes program instructions executable on a computer system for performing a computer-implemented method. The computer-implemented method includes using electrical information for a device being fabricated on a wafer to perform one or more defect-related functions. The one or more defect-related functions include one or more post-mask, defect-related functions.

The carrier medium described above may be further configured as described herein. The steps of the computer-implemented method may be further performed as described herein. In addition, the computer-implemented method for which the program instructions are executable may include any other step(s) of any other method(s) described herein.

An additional embodiment relates to a system configured to perform a computer-implemented method. The system includes a computer system configured to perform the computer-implemented method. The computer-implemented method includes using electrical information for a device being fabricated on a wafer to perform one or more defect-related functions. The one or more defect-related functions include one or more post-mask, defect-related functions.

The system described above may be further configured as described herein. The steps of the computer-implemented method may be further performed as described herein. In addition, the computer-implemented method performed by the computer system may include any other step(s) of any other method(s) described herein.

BRIEF DESCRIPTION OF THE DRAWINGS

Further advantages of the present invention may become apparent to those skilled in the art with the benefit of the following detailed description of the preferred embodiments and upon reference to the accompanying drawings in which.

Figure 1:
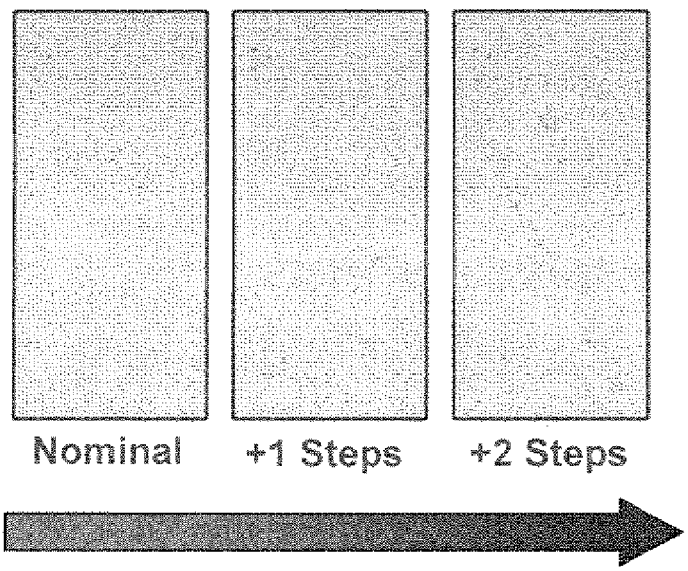
FIG. 1 is a schematic diagram illustrating one example of hot spots detected at various process window conditions.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

As used herein, the term "wafer" generally refers to substrates formed of a semiconductor or non-semiconductor material. Examples of such a semiconductor or non-semiconductor material include, but are not limited to, monocrystalline silicon, gallium arsenide, and indium phosphide. Such substrates may be commonly found and/or processed in semiconductor fabrication facilities.

A wafer may include one or more layers formed upon a substrate. For example, such layers may include, but are not limited to, a resist, a dielectric material, a conductive material, and a semiconductive material. Many different types of such layers are known in the art, and the term wafer as used herein is intended to encompass a wafer including all types of such layers.

One or more layers formed on a wafer may be patterned or unpatterned. For example, a wafer may include a plurality of dies, each having repeatable patterned features. Formation and processing of such layers of material may ultimately result in completed devices. Many different types of devices such as integrated circuits (ICs) may be formed on a wafer, and the term wafer as used herein is intended to encompass a wafer on which any type of device known in the art is being fabricated.

Although embodiments are described herein with respect to wafers, it is to be understood that the embodiments may be used for another specimen such as a reticle, which may also be commonly referred to as a mask or a photomask. Many different types of reticles are known in the art, and the terms "reticle," "mask," and "photomask" as used herein are intended to encompass all types of reticles known in the art.

The term "design data" as used herein generally refers to the physical design (layout) of an IC and data derived from the physical design through complex simulation or simple geometric and Boolean operations. In addition, an image of a reticle acquired by a reticle inspection system and/or derivatives thereof can be used as a "proxy" or "proxies" for the design data. Such a reticle image or a derivative thereof can serve as a substitute for the design layout in any embodiments described herein that use design data. The design data may include any other design data or design data proxies described in commonly owned U.S. patent application Ser. Nos. 11/561,735 by Kulkarni et al. and 11/561,659 by Zafar et al., both of which were filed on Nov. 20, 2006 and which are incorporated by reference as if fully set forth herein.

One embodiment of a computer-implemented method includes using electrical information for a device being fabricated on a wafer to perform one or more defect-related functions. The one or more defect-related functions include one or more post-mask, defect-related functions. In this manner, the methods described herein can be used for applications of electrical information (e.g., critical path information) in the post-mask environment. In some currently used systems and methods, critical path information is used in the pre-mask environment by using knowledge about the critical paths to optimize the design before the reticle mask is generated.

In one embodiment, the electrical information includes critical path information. The critical path information used in the method may be stored in any suitable data structure in any suitable format. The critical path information may be acquired from a system configured to perform the method, a system other than that configured to perform the method, or a method other than the embodiments of the method described herein. In this manner, the method may use critical path information generated by another source. Such critical path information may be generated or acquired in any suitable manner (e.g., using design data for the device, using layout information for the device, using electrical information for the device, using connectivity information for the device, using circuit information for the device, etc.). Alternatively, the critical path information may be generated by the method using electrical information about the device such as design data stored in a data structure such as a database or any other information described herein.

In one embodiment, the critical path information is acquired from netlist information for the device. The critical path information may be acquired from the netlist information for the device in any suitable manner. Although the critical path information may be acquired from the netlist information, the netlist is the connections between cells and does not include the electrical connections (or criticality) of the cells themselves. Thus, the netlist is insufficient to fully describe the electrical information in the design. The critical path information may be acquired from the netlist information by the method described herein. Alternatively, the critical path information may be acquired from the netlist information by a system configured to perform the method, another method, or a system other than that configured to perform the method.

Some embodiments include real time assessment (estimation or determination) of device performance using defect inspection data to analyze yield impact, timing delay, power leakage, resistance-capacitance (RC) variation, or some combination thereof. For example, in one embodiment, the one or more defect-related functions include determining performance of the device using defect inspection data acquired for the wafer and the electrical information. The defect inspection data may be acquired for the wafer using any suitable inspection process and inspection system such as those described herein. For example, the defect inspection data may be acquired using a bright field (BF) inspection system, a dark field (DF) inspection system, an electron beam-based inspection system, or any other suitable inspection system known in the art. The defect inspection data may also include any information generated during inspection of the wafer or by an inspection system used to inspect the wafer. For example, the defect inspection data may include defect locations reported by the inspection system, defect sizes reported by the inspection system, images of the defects such as patch images generated by the inspection system, or any other data, signals, or images generated by the inspection system.

The performance of the device may include any electrical parameter(s) of the device (e.g., timing, speed, drive current, signal integrity, and power distribution of the device). For example, the performance of the device may be determined based on the critical path information, one or more attributes of the defects detected on the wafer, one or more other attributes of the design of the device, or some combination thereof. The one or more attributes of the defects may include, for example, dimension in the x direction (e.g., width), dimension in the y direction (e.g., length), dimension in the z direction (e.g., height), shape, brightness, contrast, polarity, texture, one or more attributes of the results of the inspection in which the defects were detected, one or more parameters of the inspection in which the defects were detected, or some combination thereof. The one or more attributes of the defects may be determined in any suitable manner. The one or more attributes of the design of the device may include, for example, redundancy, netlist, dimensions of features in the design, density of features in the design, connectivity of features in the design, or some combination thereof. The one or more attributes of the design of the device may be determined in any suitable manner.

The performance of the device may be determined in a number of different manners. For example, the performance of the device may be determined based on any of the information described above by using the information to simulate the performance of the device. In addition, a range of performances may be simulated (e.g., to estimate the probability that a defect or a group of defects will cause electrical performance to exceed a defined limit. In another example, the performance of the device may be determined using any of the information described above with a correlation between experimental failure analysis (FA) or other electrical test results acquired for the device fabricated on other wafers and one or more attributes of defects detected on the other wafers.

In another embodiment, the one or more defect-related functions include using the electrical information and defect inspection data acquired for the wafer in real time to determine performance of the device. Determining the performance of the device in real time in this embodiment may, therefore, be performed during inspection of the wafer. For example, the performance of the device may be determined for individual defects after detection of the individual defects. In particular, after detection of an individual defect, the performance of the device may be determined for that individual defect even if the inspection process is still being performed on the wafer. In this manner, the performance of the device may be determined for defects during the inspection process before inspection of the entire wafer has been completed. Determining the performance of the device in real time may be performed during other processes in a similar manner. For example, the performance of the device may be determined in real time during a defect review process and/or a metrology process using output acquired during the process(es) for defects on the wafer in combination with the electrical information and possibly any other design and/or defect information described herein.

In an additional embodiment, the one or more defect-related functions include determining potential yield impact of defects on the device using defect inspection data acquired for the wafer and the electrical information. The defect inspection data may include any of the defect inspection data described herein and may be acquired as described herein. In one such embodiment, the one or more defect-related functions include using the critical path information and defect inspection data acquired for the wafer to determine potential yield impact of defects, detected by inspection of the wafer, on the device. For example, the potential yield impact of the defects on the device may be determined or predicted based on the critical path information, one or more attributes of the defects, one or more attributes of the design of the device, any other suitable information, the performance of the device, which may be determined as described above, or some combination thereof. The critical path information, the attribute(s) of the defects, and the attribute(s) of the design may include any such information described herein.

In one example, the critical path information, attribute(s) of the design such as feature size, pattern density, etc., the pattern failure caused by the defects, the locations of the defects (e.g., on top of a layer, embedded in a layer, etc.), one or more attributes of the defects such as defect size, or any other suitable information may be used to determine a likelihood that a defect will kill the device and/or alter one or more electrical parameters of the device and thereby impact yield. For example, the critical path is the path where timing of the device, for example, would suffer if there was a small pattern defect. The small defect in another part of the circuit would have a much lower impact on timing. So the defect in the critical path impacts the parametric yield (or bin/sort of how many working devices on the wafer are fact) not the typical device yield (how many defects on a wafer work).

In this manner, the one or more defect-related functions may include using critical path information (e.g., from netlist) to identify potential yield impact of defects detected during inspection. Traditionally, understanding of yield impact is determined based on limited information such as defect attributes (e.g., size, type, etc.) but not on whether the defect is occurring on or near a critical path or a non-critical path. As such, a defect can be correlated to yield or parametric data, but generating correlations in such a manner is disadvantageous because the methods generally take a substantially long time to complete the cycle (e.g., from defect detection to FA). The methods described herein can determine the potential yield impact of defects relatively quickly and, therefore, the potential yield impact may be determined in real time.

The potential yield impact may be determined for individual defects, individual groups of defects, or all of the defects detected in the device area on the wafer. The individual groups of defects may be generated by binning defects based on design data proximate to positions of the defects in design data space, and such binning may be performed as described in the above-referenced patent applications by Kulkarni et al. and Zafar et al. In addition, the defects in the device area on the wafer may be determined as described in these patent applications. Furthermore, the positions of the defects with respect to critical and non-critical paths of the device may be determined using methods described in these patent applications (e.g., by aligning the inspection data to the design data and determining the positions of the defects in design data space based on results of the aligning step, which can be used to determine the positions of the defects with respect to critical paths, non-critical paths, and other features of the design of the device).

In a further embodiment, the one or more defect-related functions include using the electrical information and defect inspection data acquired for the wafer in real time to determine potential yield impact of defects on the device. Determining potential yield impact of the defects may, therefore, be performed in real time during inspection of the wafer. For example, the potential yield impact of individual defects may be determined for each defect after each defect has been detected. Determining the potential yield impact in real time may be further performed as described herein and during other process(es) as described herein.

In another embodiment, the one or more defect-related functions include determining electrical relevancy of defects detected on the wafer. For example, the one or more defect-related functions may include using electrical critical path and defect inspection data to determine electrical yield relevancy. The electrical critical path and defect inspection data may include any such information and data described herein. In this manner, the one or more defect-related functions may include using critical path information to understand electrical relevancy of defect data. For example, defects that are detected on or near a critical path may be determined to have a higher electrical relevancy than defects that are not detected on or near a critical path. The positions of the defects with respect to critical paths in the device may be determined as described above. However, not all defects that are located on or near a critical path may be highly electrically relevant. For instance, defects that are relatively small in size and/or are located near but spaced from a critical path may be determined to have a lower electrical relevancy than defects that are relative large in size and/or are located on the critical path. The electrical relevancy of the defect may, therefore, describe how relevant the defect is to the electrical parameters of the device. However, this may not always be true. For example, the electrical relevancy of the defects may vary depending on where the defect happens, the properties of the defect, and the properties of the material the defect is displacing (e.g., a tiny defect in a liner may have much more impact than a large dielectric defect next to a metal line). In addition, or alternatively, the index may be used to rank the relevancy generally, which does not have to be perfect and is better than not ranking at all. The electrical parameters of the device may include any of the electrical parameters described herein.

In one such instance, the electrical relevancy may be determined using one or more rules or one or more algorithms that are based on attributes of the defects, attributes of the critical path information, possibly other information about the design of the device, or any other variables that may affect if and how the defect alters one or more electrical parameters of the device. In addition, the sensitivities of the electrical parameters of the device to changes in the different variables may be used to weight the variables differently in the rules or algorithms such that the electrical relevancies are determined taking into account the importance of the different variables. In this manner, the rules or algorithms may be used to determine a likelihood that a defect will alter one or more electrical parameters of the device. Defects that have a higher likelihood of altering the one or more electrical parameters of the device may be assigned a higher electrical relevancy than defects that have a lower likelihood of altering the one or more electrical parameters.

The one or more defect-related functions may also include modeling electrical parameters of the device about a defect location and determining electrical relevancy of a defect at the defect location based on results of the modeling. In this manner, the results of the modeling step may be used to determine electrical relevancy of the defect. For example, the results of the modeling step may be used to determine how the defect alters one or more electrical parameters of the device being fabricated using the design.

Modeling the electrical parameters of the device in this embodiment may be performed using any appropriate method or system known in the art. The electrical parameters of the device that are modeled may include any one or more electrical parameters of the device. The electrical relevancy of the defect may be determined using the modeled electrical parameters and the as-designed electrical parameters. For example, the modeled electrical parameters may be compared to the as-designed electrical parameters to determine the degree to which the defect alters the electrical parameters. The electrical relevancy may then be determined based on the degree to which the defect alters the electrical parameters (e.g., a defect that alters the electrical parameters to a large degree is more electrically relevant than a defect that alters the electrical parameters to a lesser degree). The electrical relevancy may be determined in a similar manner using the modeled electrical parameters and a range of suitable electrical parameters of the device. For example, the modeled electrical parameters may be compared to this range, and where the modeled electrical parameters fall within or outside of this range may be used to determine electrical relevancy. In one such example, if the modeled electrical parameters are near or outside of the acceptable range, the defect may be determined to be more electrically relevant than if the modeled parameters are inside of the acceptable range. The electrical relevancy may also be determined based, at least in part, on information from a number of different sources including, but not limited to, simulation, optical inspection results, defect review results, electrical testing results, or some combination thereof.

In an additional embodiment, the one or more defect-related functions include determining timing delay of the device due to defects detected on the wafer using defect inspection data acquired for the wafer and the electrical information. The timing delay of the device due to the defects may be determined as described above (e.g., in which timing or timing delay is determined as an electrical parameter of the device). The timing delay may be determined based on the critical path information, the defect inspection data, and any other information as described herein (e.g., in which timing or timing delay is determined as an electrical parameter of the device). In a further embodiment, the one or more defect-related functions include using the electrical information and defect inspection data acquired for the wafer in real time to determine timing delay of the device due to defects detected on the wafer. The timing delay of the device due to the defects may be determined in real time as described further herein.

In one embodiment, the one or more defect-related functions include determining power leakage of the device due to defects detected on the wafer using defect inspection data acquired for the wafer and the electrical information. The power leakage of the device due to the defects may be determined as described above (e.g., in which power or power leakage is determined as an electrical parameter of the device). In addition, the power leakage may be determined based on the critical path information, the defect inspection data, and any other information as described herein (e.g., in which power or power leakage is determined as an electrical parameter of the device). In another embodiment, the one or more defect-related functions include using the electrical information and defect inspection data acquired for the wafer in real time to determine power leakage of the device due to defects detected on the wafer. The power leakage of the device due to the defects may be determined in real time as described further herein. In a similar manner, the one or more defect-related functions may include determining cross talk due to the defects on the wafer using defect inspection data acquired for the wafer and the electrical information. Determining the cross talk may or may not be performed in real time.

In an additional embodiment, the one or more defect-related functions include determining RC variation of the device due to defects detected on the wafer using the electrical information and defect inspection data acquired for the wafer. The RC variation of the device may be determined as described above. In addition, the RC variation of the device may be determined based on the critical path information, defect inspection data, any other information, or some combination thereof as described further herein. For example, the critical path information and defect inspection data may be used in combination with information about all defects, relatively accurate sizes and locations of the defects in three dimensions (e.g., x, y, and z), information about the processing at the locations of the defects such as thicknesses and variations in material properties (e.g., dielectric constant) across the entire device, and defect properties to determine RC variation. Such information may be used with a model to introduce all of the defects across the entire device to simulate the electrical performance. The RC or other properties are a function of frequency so the output from the model may be a curve and not a single value. The curve may then be converted to a classification. In addition, since circuits are three-dimensional by nature, multiple inspection layer results may be input to the model used to determine the RC or other properties. The one or more defect-related functions may include using the electrical information and defect inspection data acquired for the wafer in real time to determine RC variation of the device due to defects detected on the wafer. The RC variation of the device due to the defects may be determined in real time as described further herein.

One benefit of the embodiments described herein is that work in progress (WIP) at risk may be reduced by using electrical information to model electrical performance instead of relying solely on electrical test data to measure the performance. In contrast, relying solely on electrical test data to measure the performance can take many weeks before an issue is discovered putting many wafers potentially at risk.

In some embodiments, the one or more defect-related functions include identifying critical defects on the wafer. For example, the one or more defect-related functions may include using critical path information (e.g., from netlist) to identify critical defects. In one such example, the critical path information may be used to determine if the defects are located on or near critical paths of the device. Defects that are located on or near critical paths of the device may be identified based on locations of the critical paths in the device and locations of the defects with respect to the device. The locations of the defects with respect to the device or design data of the device may be determined as described in the above-reference patent applications by Kulkarni et al. and Zafar et al. In this manner, the locations of the defects with respect to the device may be compared to the locations of the critical paths within the device, and defects that are located on or near (e.g., within a certain predetermined range of) the critical paths may be identified as critical defects or potentially critical defects by the method.

In another embodiment, the one or more defect-related functions include separating defects detected in areas of the wafer corresponding to electrically sensitive areas of the device from other defects detected on the wafer. For example, the one or more defect-related functions may include using critical path information to separate defects in electrically sensitive areas. In one such example, the critical path information may be used to determine electrically sensitive areas in the device. In particular, areas of the device that include one or more critical paths may be determined as electrically sensitive areas of the device. In addition, areas of the device that do not include one or more critical paths may be determined as non-electrically sensitive areas of the device. In to this manner, defects that are located in the electrically sensitive areas may be separated from defects that are not located in the electrically sensitive areas. Determining if the defects are located in electrically sensitive areas may be performed as described above.

Separating the defects in this manner may be advantageous for a number of reasons. For instance, separating the defects as described above may be performed prior to further processing of the inspection data or processes performed on the defects. In particular, the results of separating the defects as described above may be used for defect sampling such that only defects located in electrically sensitive areas are sampled for review and/or metrology. In another instance, the defects may be separated as described above prior to determining the yield impact of the defects such that the yield impact may be determined only for defects located in electrically sensitive areas. In addition, the electrical test performed on the device may be tailored based on the distribution of the defects found.

In an additional embodiment, the one or more defect-related functions include identifying one or more inspection areas on the wafer. For example, the one or more defect-related functions may include using critical path information (e.g. from netlist) to identify inspection area. In one such example, the critical path information and information about how the device is fabricated on the wafer (e.g., orientation and layout of dies on the wafer) may be used to determine the locations of critical paths on the wafer. The inspection areas on the wafer may then be selected based on the locations of the critical paths on the wafer. For example, the inspection areas on the wafer may be selected to include only areas on the wafer in which one or more critical paths are located. The inspection areas may also be selected such that the inspection areas do not include areas on the wafer in which no critical paths are located. In this manner, the area on the wafer that is inspected may be limited to areas in which electrically critical or electrically relevant defects may be located.

Such inspection is advantageous for a number of reasons. For example, such inspection may be performed quicker than inspecting the entire wafer. In addition, such inspection will detect fewer defects that are not of interest such as nuisance defects, defects that are not electrically critical, and/or defects that are not electrically relevant. As such, post-processing of the inspection results may be performed much quicker and much more accurately since the signal-to-noise ratio (S/N) of the inspection results for potential defects of interest (DOI) will be higher due to the elimination of detection of a substantial number of defects not of interest. Furthermore, different parameters for inspection of different inspection areas on the wafer may be determined based on the critical path information possibly in combination with any other information described herein. The different parameters may include, for example, different sensitivities.

The methods described herein may also include creating inspection recipes using design data as described in commonly assigned U.S. Patent Application Ser. No. 60/870,724 by Duffy et al. filed Dec. 19, 2006, which is incorporated by reference as if fully set forth herein. The methods described herein may include any step(s) of any method(s) described in this patent application. In addition, systems described herein may be further configured as described in this patent application. Furthermore, the methods described herein may include performing any of the step(s) described herein using any of the information described in this patent application in combination with any of the information described herein.

The one or more defect-related functions may also include metrology setup. For example, in one embodiment, the one or more defect-related functions include identifying critical metrology sites on the wafer. For example, the defect-related function(s) may include using critical path information (e.g., from netlist) to identify critical metrology sites. In another embodiment, the one or more defect-related functions include performing metrology in areas of the wafer corresponding to relevant areas of the device. For example, the critical path information can be implemented in metrology systems such as those commercially available from KLA-Tencor, San Jose, Calif., to perform metrology in the relevant areas of semiconductor devices. The critical metrology sites and areas of the wafer corresponding to relevant areas of the semiconductor devices may be determined as described above and is advantageous for at least the reasons described above. In particular, performing metrology only in critical metrology sites and areas of the wafer corresponding to relevant areas of the semiconductor devices will dramatically improve the throughput of the metrology process. In addition, different parameters of the metrology process may be selected for use at different critical metrology sites such as different measurements to be performed, different sampling, different parameters of the measurements to be performed, or some combination thereof.

The metrology process may include any suitable metrology process, which may include performing any suitable measurements using any suitable metrology system. For example, the metrology process may include measuring critical dimension (CD) using a scatterometry system. In another example, the metrology process may include measuring roughness using an atomic force microscope (AFM). In yet another example, the metrology process may include measuring profile of the defects using a scanning electron microscope (SEM). In addition, the metrology process may include performing one or more measurements of the defects and two or more different measurements of the defects. One of the reasons that metrology may be performed may be to improve estimates by reducing the error in the input to a model used to perform estimates based on information about the defects.

In one embodiment, the one or more defect-related functions include separating metrology variations measured in areas of the wafer corresponding to electrically sensitive areas of the device from other measured metrology variations. For example, the one or more defect-related functions may include using critical path information to separate metrology variations in the electrically sensitive areas. The electrically sensitive areas of the device may be determined as described further herein. The positions of the areas on the wafer in which the metrology variations were measured may be determined with respect to the electrically sensitive areas of the device as described further herein. In this manner, the positions of metrology sites with respect to critical paths or other features in the device may be determined and used to separate the metrology variations measured in electrically sensitive areas of the device from variations measured in non-electrically sensitive areas of the device. Separating the metrology variations in electrically sensitive areas from metrology variations in non-electrically sensitive areas may be performed such that the metrology variations in the electrically sensitive areas can be analyzed separately from other metrology variations.

In another embodiment, the one or more defect-related functions include determining electrical relevancy of metrology data acquired for the wafer. For example, the one or more defect-related functions may include using critical path information to understand electrical relevancy of metrology data. In one such example, metrology data acquired on or near one or more critical paths of the device may be assigned a higher electrical relevancy than metrology data that is not acquired on or near a critical path of the device. The position on the wafer at which the metrology data was acquired may be determined with respect to critical paths formed on the wafer as described further herein. In this manner, the positions of the metrology sites with respect to critical paths or other features in the device may be determined and used to determine the electrical relevancy of the metrology data acquired at individual metrology sites. The metrology data may include results of any metrology process or processes described herein.

In an additional embodiment, the electrical information includes critical path information, and the critical path information is generated by an electronic design automation (EDA) tool. For example, the critical path information may be available from EDA tools such as Blaze MO™ Optimization Software commercially available from Blaze DFM, Inc., Sunnyvale, Calif., and tools commercially available from Cadence Design Systems, Inc., San Jose, Calif.

In one embodiment, the electrical information includes critical path information, and the one or more defect-related functions include defect sampling in which only defects on the wafer located on or near critical paths in the device are selected for review. In this manner, the one or more defect-related functions may include using critical path information to create sampling to review only the defects that are on or near the critical paths. The defects that are located on or near the critical paths in the device may be identified as described herein. Sampling the defects in such a manner may also be performed for other processes such as metrology. Sampling the defects in such a manner is advantageous since defect review results that are particularly relevant to the electrical parameters of the device can be acquired in a relatively short amount of time since the defects that are not located on or near critical paths in the device are not selected for review thereby increasing the relevancy of the results and the turnaround time of review.

In another embodiment, the electrical information includes critical path information, and the one or more defect-related functions include overlaying the critical path information with defect inspection data acquired for the wafer and using results of the overlaying step to identify critical defects on the wafer for review. In this manner, a sequence of analysis steps performed by the method may include defect inspection, overlay with critical path, and identity critical defects to review. Overlaying the critical path information may include determining the position of the defect inspection data in design data space as described further herein and overlaying the defect inspection data in design data space coordinates with the critical path information at the same design data space coordinates. The critical defects may be identified as defects that are located on or near one or more critical paths. The defects identified as critical defects may be selected for review while defects not identified as critical defects may not be selected for review. Such defect sampling is advantageous for at least the reasons described herein. In addition, such defect sampling may be performed for one or more other processes performed on the defects such as metrology.

In one embodiment, the method includes using optimized design data for the device to describe defects detected on the wafer by error budget. For example, the method may include using optimized graphical data stream (GDS) data (e.g., Blaze MO output) to describe defect by error budget. In a similar manner, optimized GDS data may be used to describe each critical path by critical error budget, i.e., if the defect or a collection of defects exceeds the critical budget the chip will be slower, etc. In this manner, this approach is not limited to the design optimization use case. In another embodiment, the method includes evaluating optimization of design data for the device by searching the design data for patterns of interest (POI), the POI include patterns corrected and not corrected by the optimization, and the method includes comparing a failure rate of corrected and non-corrected patterns in the design data for the device. For example, the method may include confirming optimization of design data for the device by searching the design data for one or more POI. Searching the design data for one or more POI may be performed in any suitable manner. For example, searching the design data for one or more POI may be performed as described in the above-reference patent applications by Kulkarni et al. and Zafar et al. In addition, the POI may be selected or identified as described in this patent application.

In this manner, the method may include confirming optimization by Blaze through use of POI search. For example, the POI search may identify instances of the POI in the design data, and the output of the optimization by Blaze may be used to determine if all or some of the instances of the POI have been optimized. In this manner, the method may include verification or analysis of optimization of the design data and possibly feedback control of the optimization process. In addition, the method may include comparing a failure rate of corrected and non-corrected patterns in design data for the device. For example, the method may include confirming optimization by Blaze through use of POT search, which may be performed as described above, and comparing the failure rate of corrected vs. non-corrected patterns. The failure rate may be determined in any suitable manner (e.g., using defect inspection data and positions of defects detected on one or more wafers with respect to the corrected and/or non-corrected patterns, which may be determined as described above).

In one embodiment, the one or more defect-related functions include creating a systematic pareto by critical and non-critical areas of the device to identify critical and non-critical systematic defects on the wafer. In this manner, the one or more defect-related functions may include systematic pareto by critical and non-critical area thereby identifying critical systematic defects. The critical and non-critical areas may be determined as described herein (e.g., critical areas may include areas in which one or more critical paths are located and non-critical areas may include areas in which no critical paths are located). Systematic pareto may include comparing the positions of the critical and/or non-critical areas to positions of the systematic defects to identify the systematic defects located in critical and/or non-critical areas. Systematic defects located in critical areas may then be identified as critical systematic defects while systematic defects located in non-critical areas may be identified as non-critical systematic defects.

In another embodiment, the electrical information includes critical path information, and the one or more defect-related functions include separating systematic defects detected on the wafer located in critical paths of the device from systematic defects detected on the wafer located in non-critical paths of the device. In this manner, the critical path information may be used to separate critical and non-critical systematic defects. The systematic defects may be identified in any suitable manner. For example, defects detected on the wafer may be identified as systematic defects as described in the above-referenced patent applications by Kulkarni et al. and Zafar et al. The systematic defects detected on the wafer may be determined to be located on or near critical or non-critical paths of the device as described above. Separating the systematic defects located in critical paths from systematic defects located in non-critical paths is advantageous for at least the reasons described further herein. In addition, separating the systematic defects in this manner is particularly advantageous for systematic defects that impact electrical performance.

In an additional embodiment, the electrical information includes critical path information, and the one or more defect-related functions include separating random defects detected on the wafer located in critical paths of the device from random defects detected on the wafer located in non-critical paths of the device. In this manner, the critical path information may be used to separate critical and non-critical random defects. The random defects may be identified in any suitable manner. For example, defects detected on the wafer may be identified as random defects as described in the above-referenced patent applications by Kulkarni et al. and Zafar et al. Random defects may be separated in this embodiment as described above with respect to separation of systematic defects. Separating random defects located in critical paths from random defects located in non-critical paths is advantageous for at least the reasons described herein.

In one embodiment, the one or more defect-related functions are performed for defects detected on the wafer by BF inspection. For example, the methods described herein can be implemented on BF inspection systems such as those commercially available from KLA-Tencor. In addition, the methods described herein may be used with such systems and in conjunction with design-based binning (DBB) methods, which may be performed as described in the above-reference patent applications by Kulkarni et al. and Zafar et al., as a way to separate systematic and random defects in critical and non-critical paths.

In some embodiments, the electrical information includes critical path information, and the one or more defect-related functions include using the critical path information to setup a metrology process for the wafer such that changes in CDs of features of the device on the wafer are measured and can be correlated to parametric performance of the device. In this manner, the one or more defect-related functions may include using critical path information to setup metrology where any change in CDs is important and enable users to correlate to parametric performance. The metrology process may be setup in this embodiment as described further herein. In addition, the change in CDs may be correlated to parametric performance of the device as described further herein.

The methods described herein may be used to apply critical path information to defect inspection, review, and metrology. For example, in one embodiment, the one or more defect-related functions include inspection of the wafer. Inspection of the wafer may be performed based on the critical path information as described herein. In an additional embodiment, the one or more defect-related functions include defect review of the wafer. Defect review may be performed based on the critical path information as described herein. For example, the defects that are reviewed may be determined based on the critical path information as described herein. In addition, one or more other parameters of review may be selected and/or altered based on the critical path information described herein. The one or more parameters of review that are selected and/or altered based on the critical path information may include any data acquisition parameters (e.g., imaging parameters) and/or any data processing parameters (e.g., classification parameters) of the review process. In a further embodiment, the one or more defect-related functions include metrology of the wafer. Metrology of the wafer may be performed based on the critical path information as described further herein.

Embodiments described herein may also include inline defect classification of memory failure modes, which is also referred to herein as "inline bitmapping." For example, in one embodiment, the one or more defect-related functions include, during inspection of the wafer, classifying defects detected on the wafer into different memory-specific failure modes. In particular, the methods described herein can be used to provide a method to classify defects detected by wafer inspection systems such as those commercially available from KLA-Tencor during wafer inspection time into different memory (e.g., DRAM, Flash, SRAM) specific failure modes such as single-bit failure, double-bit failures, bit-line failure, and word-line failure. For example, as described further herein, design context can be used to classify memory failure modes during wafer inspection time.

In one embodiment, the one or more defect-related functions include classifying defects detected on the wafer into different memory-specific failure modes, and the method includes altering a memory redundancy design optimization strategy based on results of classifying the defects. For example, this classification will enable early warning of relatively low yielding wafers as well as better memory redundancy design optimization strategy.

In another embodiment, the one or more defect-related functions include classifying defects detected on the wafer into different memory-specific failure modes, and the method includes determining testing to be performed on the wafer based on results of classifying the defects. For example, while such inline classification may not show absolute yield loss, it may be used to disposition wafers for scrapping and/or to define further testing.

Traditional failure mode classification is performed after the entire wafer manufacturing process is completed, which is typically about 1 month to about 2.5 months of cycle time. Users may then overlay a defect map from different inspection layers with bitmapping results to troubleshoot the possible root cause of memory failures. Unfortunately, not every wafer is inspected inline and without a direct correlation to the defect map, users may not be able to determine and/or confirm the root cause easily. Therefore, the old method of failure mode classification does not provide early warning of low yielding wafers and better WIP planning. The old method of failure mode classification also does not enable better defect sampling and review strategy.

In one embodiment, the one or more defect-related functions include inline memory failure mode classification performed based on defect inspection data and design context surrounding defects detected on the wafer. In this manner, the one or more defect-related functions may include inline memory failure mode classification that takes into account defect inspection data such as defect location, defect size, and surrounding design context such as poly, metal, and specific layout pattern. In one embodiment, the one or more defect-related functions include inline memory failure mode classification and the inline memory failure mode classification includes registering POI in the device, performing defect inspection, retrieving GDS clips for every defect detected by the defect inspection, classifying the defects based on GDS matching with known POI, and based on defect location and defect size, classifying the defects into different failure modes. For example, the one or more defect-related functions may include the following steps: register a POI such as a single bit layout. Registering the pattern may be performed using DBB, which may be an option on some inspection systems commercially available from KLA-Tencor. In addition, DBB may be performed as described in the above-referenced patent applications by Kulkarni et al. and Zafar et al. The steps may also include performing defect inspection.

In addition, the steps may include retrieving a GDS clip for every defect detected by inspection (e.g., by an inspection system commercially available from KLA-Tencor). The steps may further include classifying defects based on GDS matching with known POI. Furthermore, the steps may include, based on defect location as well as defect size, classifying each defect into single-bit, double-bit bit-line, or word-line failure modes.

In one embodiment, the one or more defect-related functions include inline memory failure mode classification, and the inline memory failure mode classification includes associating a defect to a layer of the device and location of cells in the device to determine the failure mode of the defect. For example, a defect may be associated to its respective layer and location of cells. In the instance of a capacitor layer, the one or more defect-related functions may include identifying defect location to storage capacitor to determine single bit failure. The method may also include word line (poly) inspection. In such inspection, the one or more defect-related functions may include associating defect location to the poly line to determine column failure. The method may further include bit line inspection. In such inspection, the one or more defect-related functions may include associating the defect location to the bit line to determine row failure.

In this manner, the one or more defect-related functions may include using design data to classify defects during wafer inspection time. For example, in one embodiment, the one or more defect-related functions include separating bit failure from word-line or bit-line failure using POI. In another embodiment, the one or more defect-related functions include separating single bit failure from double-bit failure based on defect size. For example, the one or more defect-related functions may include using POI to separate bit failure from word-line or bit-line failure and/or may use defect size to separate single bit failure from double-bit failure.

The methods described above have the following advantages: inline disposition that provides better WIP planning, early detection of fatal wafers for faster yield learning, better sampling and review efficiency, and better memory redundancy design optimization. In addition, memory customers represent more than 40% of wafer inspection business, and customers want to ramp yield faster and optimize its redundancy strategy better. With the embodiments described herein, inspection systems can be used to provide high value information several weeks earlier than the current methodology and allow memory customers to inspect more layers with a higher sampling rate. Another interesting application for the embodiments described herein is for embedded SRAM products from fabless customers. Most of the time, these customers do not have the information to decide how much redundancy is required, and foundries do not know how to help these fabless customers. However, the embodiments described herein can be used to decide how much redundancy is required based on information that can easily be generated in the foundry and supplied to the customer. The embodiments described above for inline defect classification of memory failure modes may include any other step(s) of any other method(s) described herein.

In one embodiment, the electrical information includes netlist data. In another embodiment, the electrical information includes netlist data provided to an inspection system used to inspect the wafer. For example, the electrical information from design data can be made available to an inspection system. The electrical information made available can have several forms. In an additional embodiment, the electrical information includes critical timing paths in the device extracted from netlist data. In a further embodiment, the electrical information includes electrical circuit information. For example, the one or more defect-related functions may include using netlist or electrical circuit information in conjunction with electron beam inspection of wafers. The electrical information used in this embodiment may also or alternatively include any other information described herein.

In one embodiment, the one or more defect-related functions include targeted electron beam-based inspection of the wafer. For example, the one or more defect-related functions may include using electrical netlist data for targeted inspection in electron beam wafer defect inspection. In one such example, targeted inspection may include inspecting only areas of the device printed on the wafer indicated as critical by the electrical netlist data. In another such example, targeted inspection may include inspecting areas of the device printed on the wafer indicated as critical by the electrical netlist data with different parameters (e.g., higher sensitivity) than areas of the device printed on the wafer that are not indicated as critical by the electrical netlist data. In any of the embodiments described herein, electron beam-based inspection may be performed as described in commonly assigned U.S. Pat. Nos. 6,445,199 to Satya et al. and 6,921,672 to Satya et al., which are incorporated by reference as if fully set forth herein. The systems described herein may be configured as described in these patents. In addition, the methods described herein may include any other step(s) described in these patents.

In another embodiment, the one or more defect-related functions include targeted binning of defects detected by electron beam-based inspection of the wafer. For example, the one or more defect-related functions may include using electrical netlist data for targeted defect binning in electron beam wafer defect inspection. In one such example, the one or more defect-related functions may include using the electrical information for binning defects in n-type areas separately from defects in p-type areas. In another such example, targeted binning may include binning defects detected only in areas of the device printed on the wafer indicated as critical by the electrical netlist data. In an additional such example, targeted binning may include binning defects detected in areas of the device printed on the wafer indicated as critical by the electrical netlist data with different parameters than defects detected in areas of the device printed on the wafer that are not indicated as critical by the electrical netlist data. Binning the defects in such a manner may be advantageous for a number of reasons. For example, binning defects detected in different areas separately may provide binning results that are more accurate and/or that are more relevant to the performance of the device.

In some embodiments, the one or more defect-related functions include automatic care area generation for inspection of the wafer. For example, design data made available to an inspection system can be used for automatic care area generation. The care areas may be determined as described above with respect to inspection areas. In another embodiment, the one or more defect-related functions include automatic setup of inspection care areas for inspection of the wafer based on circuit electrical function of the device. The circuit electrical function of the device may be determined in any suitable manner and may include any suitable information. The care areas may include only a portion of features of the device formed on the wafer. For example, the care areas can be used to restrict inspected areas to, for example, only gates or drains of n-type transistors. In each of the embodiments for generating care areas, the one or more defect-related functions may also include selecting one or more parameters of the inspection to be performed in one or more of the care areas. Such parameter(s) may be selected as described further herein.

In one embodiment, the one or more defect-related functions include binning defects detected on the wafer based on electrical activity. This step may be performed using design data that is made available to the inspection system. The electrical activity may include electrical activity exhibited by the defects during electron beam-based inspection. In another embodiment, the one or more defect-related functions include binning defects detected on the wafer based on one or more attributes of the defects. For example, electrical aspects of the design data (such as whether a transistor is n-type or p-type or whether a wire connects to the substrate or is floating) can have a significant impact on the brightness or contrast of an electron beam image. By incorporating such knowledge into the inspection process, improved detection and binning of defects is possible. In another example, it is possible that a gate connection that is darker than normal indicates a killer defect in the gate oxide, while a gate connection that is brighter than normal indicates a nuisance defect. Therefore, such defects can be binned separately based on brightness. In an additional embodiment the one or more defect-related functions include binning defects detected on the wafer based on electrical environment of the defects. For example, the defects may be binned based on electrical activity exhibited by an area surrounding the defects (e.g., a neighborhood of the defects), which may indicate the effect that the defects have on the device.

In a further embodiment, the one or more defect-related functions include binning defects detected on the wafer based on connectivity of features of the device such that defects having different connectivity are binned into different groups of defects. For example, by identifying electrical nodes that connect to gates, these particular defects can be sorted accordingly as killer or nuisance. The connectivity of the features of the device may be determined in any suitable manner from any of the information described herein. In this manner, defects detected on or near features having different connectivity may be binned into different groups of defects.

Such binning of defects may be advantageous for a number of reasons. For example, the connectivity of the features on which the defects are located or near the defect locations may indicate the electrical relevancy, yield impact, or other attributes of the defects. Therefore, binning the defects based on the connectivity of the features of the device may result in separation of the defects into groups of defects such that different groups of defects have different electrical relevancy, different yield impact, different criticality, etc. In one embodiment, the one or more defect-related functions include binning defects detected on the wafer based on connectivity of features of the device such that nuisance defects are binned into a group different than one or more groups of non-nuisance defects. For example, metal contacts that are connected to a gate could be binned separately from other metal contacts to help sort out nuisance leakage.

In another embodiment, the one or more defect-related functions include determining if multiple electrically defective nodes are connected and binning the multiple electrically defective nodes as a single defect if the multiple electrically defective nodes are connected. For example, at metal levels, multiple nodes that are electrically connected and are electrically defective could be binned as a single defect rather than multiple independent defects.

In one embodiment, the electrical information includes critical timing paths in the device extracted from netlist data. The critical timing paths may be extracted from the netlist data in any suitable manner. In one such embodiment, the one or more defect-related functions include setup of targeted care areas for inspection of the wafer. In this manner, the one or more defect-related functions may include using timing information to drive care areas. The timing information may be used in combination with any other information described herein to drive care areas. Setting up the targeted care areas may be performed as described further herein (e.g., automatically). In another such embodiment, the one or more defect-related functions include setup of targeted care areas for inspection of the wafer performed such that only the most critical areas of the device are inspected during the inspection. In an additional such embodiment, the one or more defect-related functions include setup of targeted care areas for inspection of the wafer performed such that only the most critical areas of the device are inspected with the highest sensitivity of the inspection. In this manner, critical timing paths extracted from netlist data can be used to setup targeted care areas for inspection so that only the most critical areas of the chip are inspected (or are inspected with the highest available sensitivity).

In some embodiments, the one or more defect-related functions include using electrical connectivity information for the device to predict voltage contrast (VC) gray levels of images acquired during die-to-reference, electron beam-based inspection of the wafer and using the predicted VC gray levels to match the images (i.e., inspection images) to rendered images of design data for the device stored in a data structure. For example, in a die-to-database inspection, the electrical connectivity can be used to help predict VC gray levels to improve matching between the SEM image and the rendered database thereby increasing the accuracy of defect detection and reducing the detection of non-defect events (events detected due to errors in alignment of the images). Such matching may also be performed, for example, to determine the position of a defect with respect to one or more features in the design data during inspection and/or review. Therefore, the matching may be performed with higher accuracy, and any steps performed using the results of the matching may be performed with higher accuracy. In another embodiment, the one or more defect-related functions include rendering images of design data for the device for die-to-reference, electron beam-based inspection of the wafer and storing the rendered images in a data structure. In this manner, the method may be used for improved rendering of a database for die-to-database inspection.

In some embodiments, the one or more defect-related functions include using the electrical information to setup defect review that is focused on a subset of the defects detected on a wafer. For example, the defect review process may be setup by creating a sampling plan for review based on the electrical information. In one such example, the sampling plan may be determined based on the electrical information such that only defects in electrically critical areas of the device are selected for review or such that a greater number or higher percentage of defects in electrically critical areas of the device are selected for review. The sampling plan may be determined as described further herein. Setting up defect review that is focused on a subset of the defects may also include selecting any one or more other parameters of the defect review such as any of the parameter(s) described herein.

The embodiments of the method described above are advantageous over other methods and systems for a number of reasons. For example, many current inspection methods make no use of design data. Instead, defect detection is achieved by finding differences from die-to-die or cell-to-cell. Existing methods may also miss repeating defects and other subtle defects. In addition, it is difficult to setup recipes that focus only on specific features (e.g., n-type vs. p-type transistors). Furthermore, when defects are caught, it is only possible to bin them based on size and contrast, not based on their electrical function in the circuit.

In one embodiment, the electrical information includes electrical design information for the device being fabricated on the wafer. In another embodiment, the electrical information includes electrical design analysis. The electrical design analysis may include any analysis known in the art. The electrical information may also or alternatively include any other information described herein.

In another embodiment, the one or more defect-related functions include defect review of the wafer. Defect review of the wafer may be performed based on the electrical design information as described further herein. In addition, the one or more defect-related functions may include performing defect review using electrical design analysis. The defect review may be performed using the electrical design analysis as described further herein.

In an additional embodiment, the one or more defect-related functions include assisting defect review of the wafer in real time. In some embodiments, the one or more defect-related functions include assisting defect review of the wafer by assisting in defect classification. For example, the one or more defect-related functions may include using electrical design information for a device to assist in the defect review process in real time by assisting in classification. In this manner, the electrical information may be used to assist in defect classification. Defect classification may be performed using an automatic defect classification (ADC) method or algorithm modified to use the electrical information as a variable for determining the classification. Alternatively, defect classification may be performed using an ADC method or algorithm, and the classifications assigned by the ADC method or algorithm may be compared to the electrical information corresponding to the classified defects. In this manner, assigned classifications may be confirmed, modified, or corrected based on the electrical information. Such assisting of the defect review process may be performed in real time as described further herein. In this manner, the method can use electrical design data to enhance defect review.

In a further embodiment, the one or more defect-related functions include assisting defect review of the wafer by assisting sampling of defects for the defect review. For example, the one or more defect-related functions may include using electrical design information for a device to assist in the defect review process in real time by assisting in a sampling strategy for a given device. Assisting in sampling defects for defect review may include using the electrical information to sample the defects, which may be performed as described further herein. Such assisting of the defect review process may be performed in real time as described further herein. In this manner, the method can use electrical design data to enhance defect review.

In one embodiment, the one or more defect-related functions include making one or more decisions in real time during defect review of a defect location on the wafer. For example, the one or more defect-related functions may include making decisions in real time during defect review for any given defect location. In one such example, the one or more defect-related functions may include making one or more decisions in real time during defect review of a defect location based on the electrical design information. The one or more decisions may be made in real time as described further herein. In addition, the one or more decisions may include any decisions that can be made based on output generated during defect review. For example, the one or more decisions may include deciding a classification for a defect, deciding if metrology should be performed on a defect, deciding what type of metrology measurement(s) should be performed on a defect, etc.

In one such embodiment, the defect location is determined based on inspection of a reticle used to print a portion of the device on the wafer. For example, the locations of defects detected on the reticle may be used to determine locations on the wafer that should be reviewed for defects. The locations reviewed based on inspection results of the reticle may include locations on the wafer at which defects were and were not detected. In this manner, defect review may be used to analyze printability of defects on the reticle or a defect capture rate of the inspection process performed on the wafer. The locations of the defects at which defect review is performed may be determined in this embodiment as described further herein. For example, the locations of defects detected on the reticle may be used in combination with the electrical design information corresponding to features on the reticle on which the defects are located or located near the defects to determine which locations on the wafer should be reviewed.

In another such embodiment, the defect location is determined based on inspection of the wafer. For example, the locations of defects detected by inspection of the wafer may be used to determine defect locations at which defect review is performed. The locations of the defects at which defect review is performed may be determined in this embodiment as described further herein. For example, the locations of defects detected on the wafer may be used in combination with the electrical design information corresponding to features of the device on which the defects are located or located near the defects to determine which locations on the wafer should be reviewed.

In an additional such embodiment, the defect location is determined based on design analysis of the device performed to determine critical hot spots for defect detection or monitoring. The design analysis may include any suitable design analysis known in the art. The results of the design analysis may be used to determine critical hot spots in any suitable manner. In some such embodiments, only defect locations on the wafer corresponding to critical hot spots may be selected for defect review. In addition, locations on the wafer corresponding to critical hot spots may be selected for defect review regardless of whether defects were detected at the locations. Such defect review may be advantageously performed to analyze a defect capture rate for the inspection process, to monitor the critical hot spots, to verify the critical hot spots, etc. The locations of the defects at which defect review is performed may be determined in this embodiment as described further herein.

In the embodiments described herein, therefore, the defect location may be provided based on reticle or wafer inspection or may be provided based on design analysis of a device to determine critical hot spots for defect detection or monitoring. The decisions that are made in real time during defect review may fall into several categories such as those described below.

For example, in one embodiment, the one or more defect-related functions include determining, in real time during defect review of a defect location on the wafer, if a defect at the defect location is electrically relevant to the device. In this manner, the method can be used to make a decision about whether the defect is electrically relevant to the device. If the defect is not electrically relevant, it can be ignored. Examples of defects that can be ignored may be redundant contacts. Determining if a defect is electrically relevant to the device may be performed as described further herein.

In yet another such embodiment, the one or more defect-related functions include determining, in real time during defect review of a defect location on the wafer, if additional spot inspections of other parts of the device in the same electrical path as a defect at the defect location are to be performed to assist in determining electrical relevance of the defect. The additional "spot" inspections may essentially be localized inspections of the wafer, which may be performed in a process in which the entire wafer is not inspected. Such additional spot inspections may be performed with one or more different parameters than the inspection that was performed to initially detect the defects. The locations of the other parts of the device in the same electrical path as the defect at the defect location on the wafer may be determined, for example, using the wafer space location of the defect, information about the design data, and information about how the design data was printed on the wafer (e.g., spatial orientation of the design data printed on the wafer). In this manner, the locations of the other parts may be determined in wafer space. Alternatively, the locations of the other parts of the device in the same electrical path as the defect at the defect location may be determined in design space by determining a design data space position of the defect based on the wafer space position of the defect, comparing the design data space position of the defect to the design data in design data space to determine the design data space positions of the locations of the other parts, and determining the locations of the other parts on the wafer using the design data space positions of the other parts with a design data space to wafer space transformation. These steps may be performed as described in the above-referenced patent applications to Kulkarni et al. and Zafar et al. Results of the additional spot inspections may be used to assist in determining electrical relevance of the defect in any suitable manner.

In this manner, the method can be used to perform additional spot inspections of other parts of the device in the same electrical path to assist in determining the electrical relevance of a defect. The additional spot inspections may include spot inspections and/or reviews at the current layer or other layers in the device. For example, in one such embodiment, the one or more defect-related functions include determining, in real time during defect review of a defect location on the wafer, if additional spot inspections of other parts of the device in the same electrical path and layer as a defect at the defect location are to be performed to assist in determining electrical relevance of the defect. The additional spot inspections may be performed as described above. The locations on the wafer at which the additional spot inspections are to be performed may be determined as described herein. In another such embodiment, the one or more defect-related functions include determining, in real time during defect review of a defect location on the wafer, if additional spot inspections of other parts of the device in the same electrical path as a defect at the defect location and on layers other than a layer associated with the defect are to be performed to assist in determining electrical relevance of the defect. The additional spot inspections may be performed as described above. The locations on the wafer at which the additional spot inspections are to be performed may be determined as described herein. The layers on which the additional spot inspections are to be performed may include any one or more layers other than the layer on which the defect was detected.

In an additional such embodiment, the one or more defect-related functions include binning, in real time during defect review, reviewed defects on the wafer in a pareto chart based on the electrical information. For example, reviewed defects can be binned in a pareto chart based on electrical design information. Binning the reviewed defects in a pareto chart may be further performed as described herein. In some such embodiments, the electrical information includes analysis of the design, and the one or more defect-related functions include determining, in real time during the defect review, an electrical-based ranking of an effect on yield of one or more of the reviewed defects. For example, such design information may include analysis of the design to determine an electrical-based ranking of the effect on yield of any given defect. In one such example, the effect on yield of the one or more reviewed defects may be determined as described further herein, and defects determined to have a greater effect on yield may be assigned a higher electrical-based ranking than defects determined to have lesser effects on yield. Such electrical-based ranking results may be used to prioritize the defects for review, metrology, repair, and/or to prioritize portions of the design data located proximate to the defects for alteration and/or optimization. Such prioritization may be performed as described in the above-referenced patent applications by Kulkarni et al. and Zafar et al.

In one embodiment, the one or more defect-related functions include defect classification. For example, the one or more defect-related functions may include using electrical design information to classify a defect. In one such example, the one or more defect-related functions may include defect classification using electrical design analysis. Classifying the defects in this embodiment may be further performed as described herein.

In another embodiment, the one or more defect-related functions include identifying electrically critical hot spots in the device. For example, the one or more defect-related functions may include identifying electrically critical hot spots in the device based on the electrical design information for the device. Identifying the electrically critical hot spots may be performed as described further herein. In an additional embodiment, the one or more defect-related functions include identifying electrically critical hot spots in the device using information from a tool configured to define a process window for fabrication of the device on the wafer. The tool may include any tool configured to define a process window for fabrication of the device on the wafer experimentally and/or via simulation. For example, the tool may be configured to perform a process window qualification (PWQ) method. The tool may be configured to define a process window for any fabrication process performed on the wafer (e.g., lithography, etch, deposition, etc.). In this manner, the method can define a list of electrically critical hot spots either by itself or in conjunction with a tool which defines a process window. In one such embodiment, the electrically critical hot spots include locations at an edge of the process window for the device and critical to electrical performance of the device. In this manner, the electrically critical hot spots may be locations which are both at the edge of the process window for a given device as well as being critical to the electrical performance of the device.

In a further embodiment, the one or more defect-related functions include identifying electrically critical hot spots in the device and selecting the electrically critical hot spots for inspection, monitoring, or some combination thereof during defect review performed on the wafer. In this manner, the hot spots can be scheduled for spot inspection and/or monitoring during the defect review process. Such embodiments may also include selecting one or more parameters to be used for inspection, monitoring, or some combination thereof performed during defect review of the wafer. The one or more parameters may include any of the parameter(s) described herein and may be selected for inspection and/or monitoring of the electrically critical hot spots as described further herein.

Hot spots can also be defects on the mask. In addition, the one or more defect-related functions may include feedback of newly discovered hot spots to monitoring a mask. For example, crystal growth defects on a mask can be removed periodically with a mask clean. If the defects were to occur at a critical path, which may be determined as described further herein, the fab may want to clean the mask sooner than clean would otherwise be performed. The one or more defect-related functions may also include dispositioning the mask such as recommending mask clean, mask repair, or mask replacement based on the hot spots and/or the newly discovered hot spots.

The method may be performed in two modes depending on the information that is desired. For example, in some embodiments, the method includes generating the electrical information by processing design data for the device. Processing the design data may include any suitable processing know in the art. In one such embodiment, the design data includes physical layout information, three-dimensional structure information, netlist information, or some combination thereof. In one such embodiment, the one or more defect-related functions include determining a classification or ranking in real time for a defect on the wafer reviewed by a defect review tool. In another such embodiment, the one or more defect-related functions include using the electrical information and defect information generated by a defect review tool to determine electrical effects on the device due to defects detected on the wafer and using the electrical effects to determine a classification or ranking for the defects. The electrical effects of the defects on the device may be determined as described further herein. In addition, the classification or ranking may be determined as described further herein. Furthermore, determining the classification may essentially bin the defects into a defined class. However, the electrical effects on the device due to the defects detected on the wafer may be used to group or determine a grouping for the defects in a similar manner.

In this manner, in a first mode, a computer system configured to perform the method may process design data such as the physical layout, three-dimensional structure, and netlist information to determine a classification or ranking in real time for a given defect reviewed by a defect review tool. In this mode, the computer system may take information regarding the design as well as defect information generated from the review tool and analyze the electrical effect in real time to make a classification or ranking.

In some embodiments, the method includes, prior to defect review, generating the electrical information using design data for the device to determine locations of the most critical areas of the device in terms of electrical performance and storing the locations in a storage medium accessible by a review tool. Generating the electrical design information may be performed in any suitable manner. Determining locations of the most critical areas of the device in terms of electrical performance may be performed as described further herein. In addition, determining the locations of the most critical areas of the device in terms of electrical performance may include determining the sensitivity of yield to defects in different areas of the device, which may be performed as described in the above-referenced patent applications by Kulkarni et al. and Zafar et al. The areas of the device that are most sensitive to defects may be identified as the most critical areas of the device in terms of performance. Alternatively, the most critical areas of the device in terms of performance may be determined based on one or more attributes of the design data for the device, which may include any of the design data attribute(s) described herein.

The locations determined in this embodiment may be stored in any suitable storage medium in any suitable manner (e.g., as described further herein). The storage medium may be "available" to the review system if the storage medium can be accessed by the review system (e.g., by a transmission medium coupling a computer system of the review system to the storage medium). For example, the storage medium may include a storage medium included in the review system, a storage medium included in a different system (e.g., an inspection system) to which the computer system of the review system is coupled, or a fab database. In a similar manner, the locations of the most critical areas of the device in terms of electrical performance may be stored in a storage medium accessible by a tool that samples for review.

In one such embodiment, the one or more defect-related functions include using the locations to monitor the locations for defectivity. For example, the one or more defect-related functions may include using the locations to monitor the locations of the most critical areas of the device in terms of performance for defectivity.

In this manner, in the second mode, the design information may be analyzed before a review takes place to determine where the most critical areas are for a device in terms of electrical performance. These locations may be stored in a physical storage device and available to the review tool. The review tool can then be used to monitor these critical locations for defectivity.

In one embodiment, the one or more defect-related functions include using electrical CD margins for defect classification. For example, the one or more defect-related functions may include examining a defect that is a relatively small CD variation on a structure of the device. The CD may be measured by a defect review system and then processed along with the electrical design data to determine the consequence of the CD change on the electrical performance of a device. Any changes in the electrical performance of the device may be determined based on the CD change as described further herein. If the performance changes past some predefined threshold value, the location may be flagged as defective with a unique classification code. The predefined threshold value may be set by a designer of the device, a customer, or by the method.

In another embodiment, the one or more defect-related functions include real time defect classification based on electrical performance effects on the device due to defects detected on the wafer and sampling the defects for review based on electrical design data. In this manner, the one or more defect-related functions may include real time defect classification based on electrical performance effects of defects as well as additional sampling based on electrical design data. For example, the method may use a real time system to determine the effect of a defect on the electrical performance of the device. In this embodiment, defect classification and sampling may be performed as described further herein. In addition, sampling the defects may be performed in this embodiment for defect review and/or any other process to be performed on the defects (e.g., metrology). Furthermore, the defect classification and sampling may be performed in real time as described further herein.

In an additional embodiment, the one or more defect-related functions include determining an effect of a defect detected on the wafer on electrical performance of the device. The effect of a defect on the electrical performance of the device may be determined as described further herein. In a further embodiment, the one or more defect-related functions include using electrically critical hot spots in the device to perform defect monitoring. In this manner, the one or more defect-related functions may include using electrically critical hot spots to drive defect monitoring. In one such example, the areas of the wafer that are inspected, reviewed, and/or measured may be selected to include areas on the wafer corresponding to the electrically critical hot spots. The areas on the wafer corresponding to the electrically critical hot spots may be determined as described further herein. Such an embodiment may also include selecting one or more parameters to be used for defect monitoring at the electrically critical hot spots. In still another embodiment, the one or more defect-related functions include using the electrical information to determine additional device sampling based on a defect detected on the wafer. For example, the one or more defect-related functions may include using electrical design information to determine additional device sampling based on a defect. The additional device sampling may be determined as described further herein.

Turning now to the drawings, it is noted that the figures are not drawn to scale. In particular, the scale of some of the elements of the figures is greatly exaggerated to emphasize characteristics of the elements.

Given two or more pieces of data, a direct prediction of the effect(s) on device performance, and therefore yield, of any given defect may be determined. The information used for this determination may include the DOI, the design including the netlist, the current location within one or more process windows, and a characterization of the one or more process windows. The characterization of the one or more process windows may include the locations and other relevant information about any hot spots that appear at various locations within the process windows. For example, as shown in FIG. 1, process window hot spots may be detected at nominal process window conditions and at conditions that are +1 steps away from nominal, +2 steps away from nominal, etc. As further shown in FIG. 1, additional hot spots appear as a process drifts within the process window (e.g. away from nominal conditions). Using the combination of the DOI and the current location within the process windows, a system may determine what other known hot spots for that location within the process windows fall on the same electrical path as the DOI. Using the combination of these pieces of information, the system can predict the effect on device performance based on analysis of the other hot spots in the electrical path using one or more of the methods described below. The methods described below are just examples of possible methods of analysis, but any method of determining the additive effects of hot spots within a process window may be used.

The one or more defect-related functions may include overlaying the locations of any defects found on the wafer with the electrical path for the DOI and filtering for those which are located on known hot spots. These hot spots may then be assumed to have failed in a known manner, and the total effect on the circuit can be estimated. The implication is that the process window can be selected, which optimizes parametric yield by choosing process conditions that are least sensitive to process variation.

The one or more defect-related functions may include assuming that all known hot spots at that location in the process window have failed in a known manner. In this case, the total effect on the circuit for the DOI can be estimated.

The one or more defect-related functions may include using a defect review or metrology tool to perform a spot inspection of the known hot spots for the process window location along the electrical path for the given defect and accurately characterizing the conditions of the hot spots. In this way, the total effect on the circuit for the DOI can be estimated. Such spot inspections may be performed as described in commonly owned U.S. patent application Ser. No. 11/950,961 to Fouquet et al., filed Dec. 5, 2007, which is incorporated by reference as if fully set forth herein. The embodiments described herein may include any step(s) of any method(s) described in this patent application.

Any combination of these or other defect-related functions can be used to automatically assign a classification to a given defect based on its predicted effect on the device performance. In this manner, a yield prediction (parametric yield prediction or electrical performance prediction) can be made from a combination of design and process window. The input to the method may include the defect, design information, and the location in the process window. The analysis may include characterizing the defect, examining hot spots in the electrical path at the process window location using one or more of the following methods: assume all hot spots failed; spot inspections to determine additional defectivity; overlay of detected defects with hot spots to gauge hot spots defectivity; or some combination thereof, and characterizing the effect of defect and hot spot conditions on device performance. The output may include yield relevance of any given defect.

The embodiments of the method described above provide a number of advantages over other methods and systems. For instance, there is currently no known method to analyze a defect on a device based on the electrical design. Currently, the process is reversed such that an electrical defect is found at the end of the line and then FA is performed back to the original process. In addition, without knowing what the electrical effect of any given defect is on the final performance of the device, defects are currently viewed in terms of gross failures such as shorts or breaks. Even relatively small sizing defects of individual structures may be electrically important to a device and cannot currently be accurately classified. Furthermore, there is no current method to relate a given defect to the electrical performance of a device in real time.

All of the embodiments of the method described herein may also include storing results of the one or more defect-related functions or any other steps of the method in a storage medium. The results of the one or more defect-related functions may include any of the results described herein. In addition, the storing step may include storing results of the one or more defect-related functions in addition to any other results of any steps of any method embodiments described herein. The results may be stored in any manner known in the art. In addition, the storage medium may include any storage medium described herein or any other suitable storage medium known in the art. After the results have been stored, the results can be accessed in the storage medium and used by any of the method or system embodiments described herein. Furthermore, the results may be stored "permanently," "semi-permanently," temporarily, or for some period of time. For example, the storage medium may be random access memory (RAM), and the results of the one or more defect-related functions may not necessarily persist in the storage medium.

Each of the embodiments of the method described above may include any other step(s) of any other method(s) described herein. In addition, each of the embodiments of the method described above may be performed by any of the systems described herein.

Figure 2:
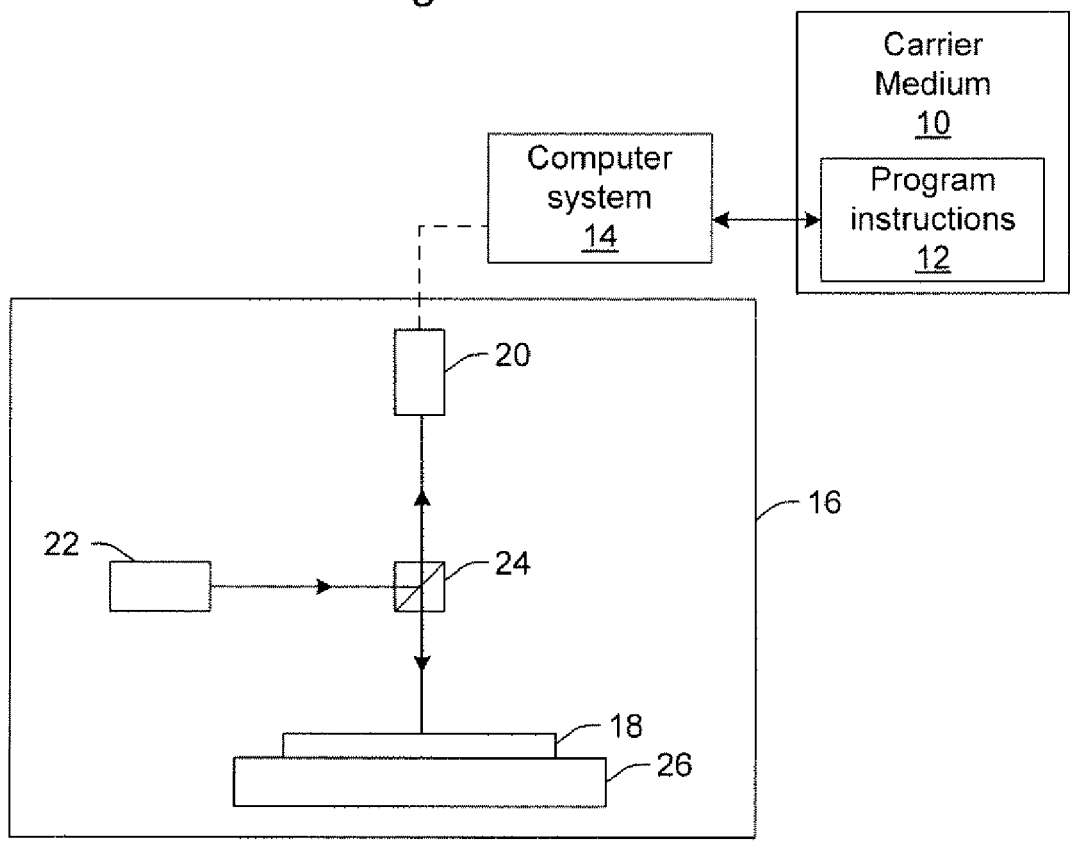
FIG. 2 is a schematic diagram illustrating a side view of various embodiments of a carrier medium that includes program instructions executable on a computer system for performing one or more embodiments of a computer-implemented method described herein and a system configured to perform one or more embodiments of a computer-implemented method described herein.

Another embodiment relates to a carrier medium that includes program instructions executable on a computer system for performing a computer-implemented method. One embodiment of such a carrier medium is shown in FIG. 2. In particular, carrier medium 10 includes program instructions 12 executable on computer system 14 for performing a computer-implemented method. The computer-implemented method includes using electrical information for a device being fabricated on a wafer to perform one or more defect-related functions. The one or more defect-related functions include one or more post-mask, defect-related functions. The computer-implemented method may perform the defect-related function(s) using any of the electrical information described further herein, and the defect-related function(s) may include any of the defect-related function(s) described herein. The computer-implemented method executable on the computer system by the program instructions may include any other step(s) of any other method(s) described herein. In addition, the carrier medium may be further configured as described herein.

Pro gram instructions 12 implementing methods such as those described herein may be transmitted over or stored on carrier medium 10. The carrier medium may be a transmission medium such as a wire, cable, or wireless transmission link. The carrier medium may also be a storage medium such as a read-only memory, a random access memory, a magnetic or optical disk, or a magnetic tape.

The program instructions may be implemented in any of various ways, including procedure-based techniques, component-based techniques, and/or object-oriented techniques, among others. For example, the program instructions may be implemented using Matlab, Visual Basic, ActiveX controls, C, C++ objects, C#, JavaBeans, Microsoft Foundation Classes ("MFC"), or other technologies or methodologies, as desired.

An additional embodiment relates to a system configured to perform a computer-implemented method. The system includes a computer system configured to perform the computer-implemented method. One embodiment of such a system is shown in FIG. 2. For example, the system may include computer system 14 configured to perform the computer-implemented method. The computer-implemented method includes using electrical information for a device being fabricated on a wafer to perform one or more defect-related functions. The one or more defect-related functions include one or more post-mask, defect-related functions. The computer system may perform the defect-related function(s) using any of the electrical information described further herein, and the defect-related function(s) may include any of the defect-related function(s) described herein. The computer-implemented method performed by the computer system may include any other step(s) of any other method(s) described herein. The system may be further configured according to any embodiment(s) described herein.

The system may be configured as a stand-alone system that does not form part of a process, inspection, metrology, review, or other tool. In such a system, computer system 14 may be configured to receive and/or acquire data or information from other systems (e.g., inspection data from an inspection system) by a transmission medium that may include "wired" and/or "wireless" portions. In this manner, the transmission medium may serve as a data link between the computer system and the other system. In addition, computer system 14 may send data to the other system via the transmission medium. Such data may include, for example, design data, context data, results of the methods described herein, inspection recipes or other recipes, or some combination thereof.

Computer system 14 may take various forms, including a personal computer system, mainframe computer system, workstation, image computer, parallel processor, or any other device known in the art. In general, the term "computer system" may be broadly defined to encompass any device having one or more processors, which executes instructions from a memory medium.

In other embodiments, however, the system includes inspection system 16. Inspection system 16 is configured to acquire defect inspection data for wafer 18. In embodiments of the system that include the inspection system, computer system 14 may be coupled to the inspection system in any manner known in the art. For example, computer system 34 may be coupled to detector 20 of inspection system 16 such that the computer system can receive inspection data generated by the detector. In addition, the computer system may receive any other output of the detector such as image data and signals. Furthermore, if the inspection system includes more than one detector (not shown), the computer system may be coupled to each detector as described above.

In one embodiment, inspection system 16 includes light source 22. Light source 22 may include any appropriate light source known in the art. Light source 22 may be configured to direct light to beam splitter 24. Beam splitter 24 may be configured to direct light from light source 22 to wafer 18 at a substantially normal angle of incidence. Beam splitter 24 may include any appropriate optical component known in the art. Light reflected from wafer 18 may pass through beam splitter 24 to detector 20. Detector 20 may include any appropriate detector known in the art. Output generated by detector 20 may be used to detect defects on wafer 18. For example, computer system 14 may be configured to detect defects on wafer 18 using output generated by the detector. The computer system may use any method and/or algorithm known in the art to detect defects on the wafer. During inspection, wafer 18 may be disposed on stage 26. Stage 26 may include any appropriate mechanical and/or robotic assembly known in the art. The inspection system shown in FIG. 2 may also include any other suitable components (not shown) known in the art.

As shown in FIG. 2, the inspection system is configured to detect light specularly reflected from the wafer. In this manner, the inspection system shown in FIG. 2 is configured as a BF inspection system. However, the inspection system may be replaced by an inspection system configured as a DF inspection system, an edge contrast (EC) inspection system, an aperture mode inspection system, or any other optical inspection system known in the art. In addition, the inspection system may be configured to perform one or more inspection modes. For example, the inspection system shown in FIG. 2 may be configured to perform DF inspection by altering an angle of incidence at which the light is directed to the wafer and/or an angle at which light is collected from the wafer. In another example, the inspection system may be configured such that one or more optical components (not shown) such as apertures may be positioned in the illumination path and the collection path such that the inspection system can perform EC mode inspection and/or an aperture mode of inspection.

Furthermore, the optical inspection system shown in FIG. 2 may include a commercially available inspection system such as the 2360, 2365, 2371, and 23xx systems that are available from KLA-Tencor. In another embodiment, the optical inspection system shown in FIG. 2 may be replaced by an electron beam inspection system. Examples of commercially available electron beam inspection systems that may be included in the system of FIG. 2 include the eS25, eS30, and eS31 systems from KLA-Tencor. The embodiments of the system shown in FIG. 2 may be further configured as described herein. In addition, the system may be configured to perform any other step(s) of any of the method embodiment(s) described herein. The embodiments of the system shown in FIG. 2 have all of the advantages of the method embodiments described above.

Further modifications and alternative embodiments of various aspects of the invention may be apparent to those skilled in the art in view of this description. For example, methods and systems for using electrical information for a device being fabricated on a wafer to perform one or more defect-related functions are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A computer-implemented method, comprising:
generating electrical information for a device being fabricated on a wafer by processing design data for the device, wherein the design data cormprises physical layout information, three-dimensional structure information, netlist information, or some combination thereof; and
using the electrical information to perform one or more defect-related functions, wherein the one or more defect-related functions comprise one or more post-mask, defect-related functions, wherein the one or more defect-related functions further comprise using the electrical information and defect information generated by a defect review tool to determine electrical effects on the device due to defects detected on the wafer and using the electrical effects to determine a classification or ranking for the defects and wherein said generating and said using the electrical information are performed using a computer system.

2. The method of claim 1, wherein the electrical information comprises critical path information.

3. The method of claim 1, wherein the one or more defect-related functions further comprise determining performance of the device using defect inspection data acquired for the wafer and the electrical information.

4. The method of claim 1, wherein the one or more defect-related functions further comprise using the electrical information and defect inspection data acquired for the wafer in real time to determine performance of the device.

5. The method of claim 1, wherein the one or more defect-related functions further comprise determining potential yield impact of defects on the device using defect inspection data acquired for the wafer and the electrical information.

6. The method of claim 1, wherein the one or more defect-related functions further comprise using the electrical information and defect inspection data acquired for the wafer in real time to determine potential yield impact of defects on the device.

7. The method of claim 1, wherein the one or more defect-related functions further comprise determining electrical relevancy of defects detected on the wafer.

8. The method of claim 1, wherein the one or more defect-related functions further comprise determining timing delay of the device due to defects detected on the wafer using defect inspection data acquired for the wafer and the electrical information.

9. The method of claim 1, wherein the one or more defect-related functions further comprise using the electrical information and defect inspection data acquired for the wafer in real time to determine timing delay of the device due to defects detected on the wafer.

10. The method of claim 1, wherein the one or more defect-related functions further comprise determining power leakage of the device due to defects detected on the wafer using defect inspection data acquired for the wafer and the electrical information.

11. The method of claim 1, wherein the one or more defect-related functions further comprise using the electrical information and defect inspection data acquired for the wafer in real time to determine power leakage of the device due to defects detected on the wafer.

12. The method of claim 1, wherein the one or more defect-related functions further comprise determining resistance-capacitance variation of the device due to defects detected on the wafer using the electrical information and defect inspection data acquired for the wafer.

13. The method of claim 1, wherein the one or more defect-related functions further comprise using the electrical information and defect inspection data acquired for the wafer in real time to determine resistance-capacitance variation of the device due to defects detected on the wafer.

14. The method of claim 1, wherein the electrical information comprises critical path information, and wherein the critical path information is acquired from netlist information for the device.

15. The method of claim 1, wherein the one or more defect-related functions further comprise identifying critical defects on the wafer.

16. The method of claim 1, wherein the one or more defect-related functions further comprise separating defects detected in areas of the wafer corresponding to electrically sensitive areas of the device from other defects detected on the wafer.

17. The method of claim 1, wherein the one or more defect-related functions further comprise identifying one or more inspection areas on the wafer.

18. The method of claim 1, wherein the one or more defect-related functions further comprise identifying critical metrology sites on the wafer.

19. The method of claim 1, wherein the one or more defect-related functions further comprise separating metrology variations measured in areas of the wafer corresponding to electrically sensitive areas of the device from other measured metrology variations.

20. The method of claim 1, wherein the one or more defect-related functions further comprise determining electrical relevancy of metrology data acquired for the wafer.

21. The method of claim 1, wherein the electrical information comprises critical path information, and wherein the critical path information is generated by an electronic design automation tool.

22. The method of claim 1, wherein the electrical information comprises critical path information, and wherein the one or more defect-related functions further comprise defect sampling in which only defects on the wafer located on or near critical paths in the device are selected for review.

23. The method of claim 1, wherein the electrical information comprises critical path information, and wherein the one or more defect-related functions further comprise overlaying the critical path information with defect inspection data acquired for the wafer and using results of said overlaying to identify critical defects on the wafer for review.

24. The method of claim 1, further comprising using optimized design data for the device to describe defects detected on the wafer by error budget.

25. The method of claim 1, further comprising evaluating optimization of design data for the device by searching the design data for patterns of interest, wherein the patterns of interest comprise patterns corrected and not corrected by the optimization, and comparing a failure rate of corrected and non-corrected patterns in the design data for the device.

26. The method of claim 1, wherein the one or more defect-related functions further comprise creating a systematic pareto by critical and non-critical areas of the device to identify critical and non-critical systematic defects on the wafer.

27. The method of claim 1, wherein the electrical information comprises critical. path information, and wherein the one or more defect-related functions further comprise separating systematic defects detected on the wafer located in critical paths of the device from systematic defects detected on the wafer located in non-critical paths of the device.

28. The method of claim 1, wherein the electrical information comprises critical path information, and wherein the one or more defect-related functions further comprise separating random defects detected on the wafer located in critical paths of the device from random defects detected on the wafer located in non-critical paths of the device.

29. The method of claim 1, wherein the one or more defect-related functions are performed for defects detected on the wafer by bright field inspection.

30. The method of claim 1, wherein the electrical information comprises critical path information, and wherein the one or more defect-related functions further comprise using the critical path information to setup a metrology process for the wafer such that changes in critical dimensions of features of the device on the wafer are measured and can be correlated to parametric performance of the device.

31. The method of claim 1, wherein the one or more defect-related functions further comprise inspection of the wafer.

32. The method of claim 1, wherein the one or more defect-related functions further comprise defect review of the wafer.

33. The method of claim 1, wherein the one or more defect-related functions further comprise metrology of the wafer.

34. The method of claim 1, wherein the electrical information comprises netlist data.

35. The method of claim 1, wherein the electrical information comprises netlist data provided to an inspection system used to inspect the wafer.

36. The method of claim 1, wherein the electrical information comprises electrical. circuit information.

37. The method of claim 1, wherein the one or more defect-related functions further comprise targeted electron beam-based inspection of the wafer.

38. The method of claim 1, wherein the one or more defect-related functions further comprise targeted binning of defects detected by electron beam-based inspection of the wafer.

39. The method of claim 1, wherein the one or more defect-related functions further comprise automatic care area generation for inspection of the wafer.

40. The method of claim 1, wherein the one or more defect-related functions further comprise automatic setup of inspection care areas for inspection of the wafer based on circuit electrical function of the device.

41. The method of claim 1, wherein the one or more defect-related functions further comprise binning defects detected on the wafer based on electrical activity.

42. The method of claim 1, wherein the one or more defect-related functions further comprise binning defects detected on the wafer based on electrical environment of the defects.

43. The method of claim 1, wherein the one or more defect-related functions further comprise binning defects detected on the wafer based on connectivity of features of the device such that defects having different connectivity are binned into different groups of defects.

44. The method of claim 1, wherein the one or more defect-related functions further comprise binning defects detected on the wafer based on connectivity of features of the device such that nuisance defects are binned into a group different than one or more groups of non-nuisance defects.

45. The method of claim 1, wherein the one or more defect-related functions further comprise determining if multiple electrically defective nodes are connected and binning the multiple electrically defective nodes as a single defect if the multiple electrically defective nodes are connected.

46. The method of claim 1, wherein the electrical information comprises critical timing paths in the device extracted from netlist data, and wherein the one or more defect-related functions further comprise setup of targeted care areas for inspection of the wafer.

47. The method of claim 1, wherein the one or more defect-related functions further comprise using electrical connectivity information for the device to predict voltage contrast gray levels of images acquired during die-to-reference, electron beam-based inspection of the wafer and using the predicted voltage contrast gray levels to match the images to rendered images of design data for the device stored in a data structure.

48. The method of claim 1, wherein the one or more defect-related functions further comprise rendering images of design data for the device for die-to-reference, electron beam-based inspection of the wafer and storing the rendered images in a data structure.

49. The method of claim 1, wherein the electrical information comprises electrical design information for the device being fabricated on the wafer.

50. The method of claim 1, wherein the electrical information comprises electrical design analysis.

51. The method of claim 1, wherein the one or more defect-related functions further comprise assisting defect review of the wafer in real time.

52. The method of claim 1, wherein the one or more defect-related functions further comprise assisting defect review of the wafer by assisting in defect classification.

53. The method of claim 1, wherein the one or more defect-related functions further comprise assisting defect review of the wafer by assisting sampling of defects for the defect review.

54. The method of claim 1, wherein the one or more defect-related functions further comprise making one or more decisions in real time during defect review of a defect location on the wafer.

55. The method of claim 1, wherein the one or more defect-related functions further comprise making one or more decisions in real time during defect review of a defect location on the wafer, and wherein the defect location is determined based on inspection of a reticle used to print a portion of the device on the wafer.

56. The method of claim 1. wherein the one or more defect-related functions further comprise making one or more decisions in real time during defect review of a defect location on the wafer, and wherein the defect location is determined based on design analysis of the device performed to determine critical hot spots for defect detection or monitoring.

57. The method of claim 1, wherein the one or more defect-related functions further comprise determining, in real time during defect review of a defect location on the wafer, if a defect at the defect location is electrically relevant to the device.

58. The method of claim 1, wherein the one or more defect-related functions further comprise determining, in real time during defect review of a defect location on the wafer, if additional spot inspections of other parts of the device in the same electrical path as a defect at the defect location are to be performed to assist in determining electrical relevance of the defect.

59. The method of claim 1, wherein the one or more defect-related functions further comprise determining, in real time during defect review of a defect location on the wafer, if additional spot inspections of other parts of the device in the same electrical path and layer as a defect at the defect location are to be performed to assist in determining electrical relevance of the defect.

60. The method of claim 1, wherein the one or more defect-related functions further comprise determining, in real time during defect review of a defect location on the wafer, if additional spot inspections of other parts of the device in the same electrical path as a defect at the defect location and on layers other than a layer associated with the defect are to be performed to assist in determining electrical relevance of the defect.

61. The method of claim 1, wherein the one or more defect-related functions further comprise binning, in real time during defect review, reviewed defects on the wafer in a pareto chart based on the electrical information.

62. The method of claim 1. wherein the one or more defect-related functions further comprise binning, in real time during defect review, reviewed defects on the wafer in a pareto chart based on the electrical information, wherein the electrical information comprises analysis of the design, and determining, in real time during the defect review, an electrical-based ranking of an effect on yield of one or more of the reviewed defects.

63. The method of claim 1, wherein the one or more defect-related functions further comprise defect classification.

64. The method of claim 1, wherein the one or more defect-related functions further comprise identifying electrically critical hot spots in the device.

65. The method of claim 1, wherein the one or more defect-related functions further comprise identifying electrically critical hot spots in the device using information from a tool configured to define a process window for fabrication of the device on the wafer.

66. The method of claim 1, wherein the one or more defect-related functions further comprise identifying electrically critical hot spots in the device using information from a tool configured to define a process window for fabrication of the device on the wafer, and wherein the electrically critical hot spots comprise locations at an edge of the process window for the device and critical to electrical performance of the device.

67. The method of claim 1, wherein the one or more defect-related functions further comprise identifying electrically critical hot spots in the device and selecting the electrically critical hot spots for inspection, monitoring, or some combination thereof during defect review performed on the wafer.

68. The method of claim 1, further comprising generating the electrical information by processing, design data for the device, wherein the design data comprises physical layout information, three-dimensional structure information, netlist information, or some combination thereof, and wherein the one or more defect-related functions further comprise determining a classification or ranking in real time for a defect on the wafer reviewed by a defect review tool.

69. The method of claim 1, further comprising prior to defect review, generating the electrical information using design data for the device to determine locations of the most critical areas of the device in terms of electrical performance and storing the locations in a storage medium accessible by a review tool.

70. The method of claim 1, further comprising prior to defect review, generating the electrical information using design data for the device to determine locations of the most critical areas of the device in terms of electrical performance and storing the locations in a storage medium accessible by a review tool, wherein the one or more defect-related functions further comprise using the locations to monitor the locations for defectivity.

71. The method of claim 1, wherein the one or more defect-related functions further comprise using electrical critical dimension margins for defect classification.

72. The method of claim 1, wherein the one or more defect-related functions further comprise real time detect classification based on electrical performance effects on the device due to defects detected on the wafer and sampling the defects for review based on electrical design data.

73. The method of claim 1, wherein the one or more defect-related functions further comprise determining an effect of a defect on the wafer on electrical performance of the device.

74. The method of claim 1, wherein the one or more defect-related functions further comprise using electrically critical hot spots in the device to perform defect monitoring.

75. The method of claim 1, wherein the one or more defect-related functions further comprise using the electrical information to determine additional device sampling based on a defect detected on the wafer.

76. The method of claim 1, wherein the one or more defect-related functions further comprise, during inspection of the wafer, classifying defects detected on the wafer into different memory-specific failure modes.

77. The method of claim 1, wherein the one or more defect-related functions further comprise classifying defects detected on the wafer into different memory-specific failure modes, and wherein the method further comprises altering a memory redundancy design optimization strategy based on results of classifying the defects.

78. The method of claim 1, wherein the one or more defect-related functions further comprise classifying defects detected on the wafer into different memory-specific failure modes, and wherein the method further comprises determining testing to be performed on the wafer based on results of classifying the defects.

79. The method of claim 1, wherein the one or more defect-related functions further comprise inline memory failure mode classification performed based on defect inspection data and design context surrounding defects detected on the wafer.

80. The method of claim 1, wherein the one or more defect-related functions further comprise inline memory failure mode classification, and wherein the inline memory failure mode classification comprises registering patterns of interest in the device, performing defect inspection, retrieving GDS clips for every defect detected by the defect inspection, classifying the defects based on GDS matching with known patterns of interest, and based on defect location and defect size, classifying the defects into different memory failure modes.

81. The method of claim 1, wherein the one or more defect-related functions further comprise separating bit failure from word-line or bit-line failure using patterns of interest.

82. The method of claim 1, wherein the one or more defect-related functions further comprise separating single bit failure from double-hit failure based on defect size.

83. The method of claim 1, wherein the one or more defect-related functions further comprise inline memory failure mode classification, and wherein the inline memory failure mode classification comprises associating a defect to a layer of the device and location of cells in the device to determine the failure mode of the defect.

84. A non-transitory computer-readable medium, comprising program instructions executable on a computer system for performing a computer-implemented method, wherein the computer-implemented method comprises;
 generating electrical information for a device being fabricated on a wafer by processing design data for the device wherein the design data comprises physical layout information, three-dimensional structure information, netlist information, or some combination thereof; and
 using the electrical information to perform one or more defect-related functions, wherein the one or more defect-related functions comprise one or more post-mask, defect-related functions, and wherein the one or more defect-related functions further comprise using the electrical information and defect information generated by a defect review tool to determine electrical effects on the device due to defects detected on the wafer and using the electrical effects to determine a classification or ranking for the defects.

85. A system configured to perform a computer-implemented method, comprising a computer system configured to perform the computer-implemented method, wherein the computer-implemented method comprises;
 generating electrical information for a device bein fabricated on a wafer by processing design data for the device, wherein the design data comprises physical layout information three-dimensional structure information netlist information, or some combination thereof; and
 using the electrical information to perform one or more defect-related functions, wherein the one or more defect-related functions comprise one or more post-mask, defect-related functions, and wherein the one or more defect-related functions further comprise using the electrical information and defect information generated by a defect review tool to determine electrical effects on the device due to defects detected on the wafer and using the electrical effects to determine a classification or ranking for the defects.

\* \* \* \* \*